(12) United States Patent
Elagin et al.

(10) Patent No.: US 7,473,773 B2
(45) Date of Patent: Jan. 6, 2009

(54) DETERMINATION OF HEPATITIS C VIRUS GENOTYPE

(75) Inventors: Vecheslav A. Elagin, Waunakee, WI (US); Scott M. Law, Madison, WI (US); Bjork Hill, Ames, IA (US)

(73) Assignee: Third Wave Technologies, Inc., Madison, WI (US)

( * ) Notice: Subject to any disclaimer, the term of this patent is extended or adjusted under 35 U.S.C. 154(b) by 313 days.

(21) Appl. No.: 11/031,487

(22) Filed: Jan. 7, 2005

(65) Prior Publication Data

US 2005/0196750 A1 Sep. 8, 2005

Related U.S. Application Data

(60) Provisional application No. 60/534,618, filed on Jan. 7, 2004, provisional application No. 60/563,629, filed on Apr. 20, 2004.

(51) Int. Cl.
C07H 21/04 (2006.01)

(52) U.S. Cl. .................... 536/24.3; 536/22.1; 536/23.1; 435/5; 435/194; 435/325

(58) Field of Classification Search ........................ None
See application file for complete search history.

(56) References Cited

U.S. PATENT DOCUMENTS

| | | | |
|---|---|---|---|
| 5,527,669 A | 6/1996 | Resnick et al. | |
| 5,614,402 A | 3/1997 | Dahlberg et al. | |
| 5,712,088 A | 1/1998 | Houghton et al. | |
| 5,714,596 A | 2/1998 | Houghton et al. | |
| 5,795,763 A | 8/1998 | Dahlberg et al. | |
| 5,843,669 A | 12/1998 | Kaiser et al. | |
| 5,846,704 A | 12/1998 | Maertens et al. | |
| 5,846,717 A | 12/1998 | Brow et al. | |
| 5,863,719 A | 1/1999 | Houghton et al. | |
| 5,882,852 A | 3/1999 | Bukh et al. | |
| 5,942,391 A | 8/1999 | Zhang et al. | |
| 5,959,092 A | 9/1999 | Miyamura et al. | |
| 5,985,557 A | 11/1999 | Prudent et al. | |
| 5,994,069 A | 11/1999 | Hall et al. | |
| 6,001,567 A | 12/1999 | Brow et al. | |
| 6,071,693 A | 6/2000 | Cha et al. | |
| 6,074,816 A | 6/2000 | Houghton et al. | |
| 6,090,543 A | 7/2000 | Prudent et al. | |
| 6,090,606 A | 7/2000 | Kaiser et al. | |
| 6,194,149 B1 | 2/2001 | Neri et al. | |
| 6,235,480 B1 * | 5/2001 | Shultz et al. | 435/6 |
| 6,297,370 B1 | 10/2001 | Cha et al. | |
| 6,348,314 B1 | 2/2002 | Prudent et al. | |
| 6,416,944 B1 | 7/2002 | Chein et al. | |
| 6,458,535 B1 | 10/2002 | Hall et al. | |
| 6,495,670 B1 | 12/2002 | Maertens et al. | |
| 6,548,244 B2 | 4/2003 | Maertens et al. | |
| 6,762,024 B2 | 7/2004 | Maertens et al. | |
| 6,881,821 B2 | 4/2005 | Simmonds et al. | |
| 2002/0183508 A1 | 12/2002 | Martens et al. | |
| 2003/0104378 A1 | 6/2003 | Allawi et al. | |
| 2003/0152591 A1 | 8/2003 | Sablon et al. | |
| 2003/0152942 A1 | 8/2003 | Fors et al. | |
| 2003/0186238 A1 | 10/2003 | Allewi et al. | |

FOREIGN PATENT DOCUMENTS

| | | |
|---|---|---|
| WO | WO 91/04262 | 4/1991 |
| WO | WO 91/14779 | 10/1991 |
| WO | WO 92/19743 | 11/1992 |
| WO | WO 97/27214 | 7/1997 |
| WO | WO 98/23774 | 6/1998 |
| WO | WO 98/42873 | 10/1998 |
| WO | WO9850403 | 11/1998 |
| WO | WO0190337 A2 | 11/2001 |
| WO | WO 01/98537 | 12/2001 |
| WO | WO 02/070755 A2 | 9/2002 |

OTHER PUBLICATIONS

Mochida et al. Biochemical and Biophysical Research Communication, Jan. 23, 2004, vol. 313, p. 1079-1085.*
Simmonds, "Variability of hepatitis C virus," P. Hepatology. Feb;21(2):570-83 (1995).
Simmonds, "Viral heterogeneity of the hepatitis C virus," P. J Hepatol.;31 Suppl 1:54-60 (1999).
Zein et al., "Hepatitis C Genotypes in Liver Transplant recipients: Distribution and 1-Year Follow-Up," Liver Transplant. Surg. 1: 354-357 (1995).
Gordon et al., "Relationship between hepatitis C genotype and severity of recurrent hepatitis C after liver tranplantation," Transplantation 63: 1419-1423 (1997).
Stuyver, et al., "Second-generation line probe assay for hepatitis C virus genotyping.," J. Clin. Micro., 34: 2259-2266 (1996).
Germer et al., "Evaluation of the TRUGENE HCV 5'NC genotyping kit with the new GeneLibrarian module 3.1.2 for genotyping of hepatitis C virus from clinical specimens," J Clin Microbiol. Oct. 2003;41(10):4855-7.
Lyamichev et al., "Polymorphism identification and quantitative detection of genomic DNA by invasive cleavage of oligonucleotide probes," Nat. Biotech., 17:292 (1999).
Hall et al., "Sensitive detection of DNA polymorphisms by the serial invasive signal amplification reaction," PNAS, USA, 97:8272 (2000).
Stuyver et al., "Typing of hepatitis C virus isolates and characterization of new subtypes using a line probe assay.," J of Gen Virol 74:1093-1102 (1993).
Lee et al., "Identification of hepatitis C viruses with a nonconserved sequence of the 5' untranslated region," J Clin Micro, 30(6):1602-04 (1992).

(Continued)

*Primary Examiner*—Bruce Campbell
*Assistant Examiner*—Agnieszka Boesen
(74) *Attorney, Agent, or Firm*—Casimir Jones, S.C.

(57) ABSTRACT

The present invention provides compositions and methods for the detection and characterization of HCV sequences. More particularly, the present invention provides compositions, methods and kits for using invasive cleavage structure assays (e.g. the INVADER assay) to screen nucleic acid samples, e.g., from patients, to determine HCV genotype.

27 Claims, 15 Drawing Sheets

OTHER PUBLICATIONS

Cha et al., "At least five related, but distinct, hepatitis C viral genotypes exist," PNAS USA, 89:7144:48 (1992).

Chan et al., "Analysis of a new hepatitis C virus type and its phylogenetic relationship to existing variants," J of Gen Virol., 73:1131-41 (1992).

Bukh et al., "Sequence analysis of the 5' noncoding region of hepatitis C virus," PNAS, USA, 89:4942-46 (1992).

Fields et al., "Unrelatedness of factor VIII-derived non-A/non-B hepatitis and hepatitis B virus," J. of Medical Virology, 11:59-65 (1983).

Bradley, "The agents of non-A, non-B viral hepatitis," Journal of Virological Methods, 10:307-319 (1985).

Yap et al., "Absence of detectable hepatitis B virus DNA in sera and liver of chimpanzees with non-A, non-B hepatitis," J. Med Virol 15:343-350 (1985).

Weiner et al., "Hepatitis delta (delta) cDNA clones: undetectable hybridization to nucleic acids from infectious non-A, non-B hepatitis materials and hepatitis B DNA," Journal of Medical Virology, 21:239-247 (1987).

Kato et al., "Japanese Isolates of the Non-A, Non-B Hepatitis Viral Genome Show Sequence Variations from the Original Isolate in the U.S.A.," Proc. Japan. Acad., 65 (Ser. B):219-223, 1989.

Kubo et al., "A cDNA fragment of hepatitis C virus isolated from an implicated donor of post-transfusion non-A, non-B hepatitis in Japan," Nucleic Acids Research, 17(24):10367-10372, 1989.

Takeuchi et al., "Hepatitis C viral cDNA clones isolated from a healthy carrier donor implicated in post-transfusion non-A, non-B hepatitis," Gene, 91:287-291, 1990.

Chapman et al., "Molecular detection and identification of enteroviruses using enzymatic amplification and nucleic acid hybridization," J Clin Microbiol, 28:843-850 (1990).

* cited by examiner

Figure 3

| | | | |
|---|---|---|---|
| SEQ ID NO: 1 | Set A/ 6G | Invader oligo | gctgcacgaaGGCTAGCGGTCTCGCAGGGGCGCGCCTAAATa |
| SEQ ID NO: 2 | Set A/ 6G | probe oligo | acggacgcggagCTCCAGACATTGGGCGGTT |
| SEQ ID NO: 3 | Set A/ 6G | probe oligo | acggacgcggagCTCCAGACATTGGGCGGG |
| SEQ ID NO: 4 | Set A/ 6G | probe oligo | acggacgcggagCTCCGGGCATCGAGC |
| SEQ ID NO: 5 | Set B/ 8T | Invader oligo | cagccGCGGGTCATCCGAGAAAGGGCCCGGCCGTCCa |
| SEQ ID NO: 6 | Set B/ 8T | Invader oligo | tggccgaggATCCAATGGAAAGGGCCCGGTCATCCa |
| SEQ ID NO: 7 | Set B/ 8T | probe oligo | acggacgcggagTGGCAATCCGGTGCACTCACC |
| SEQ ID NO: 8 | Set B/ 8T | probe oligo | acggacgcggagTGCCAATTGCGGTGTA |
| SEQ ID NO: 9 | Set C/ 7C | Invader oligo | cctgccGTGCCTCCGCAGGACTGCCAGCCGGGTAGa |
| SEQ ID NO: 10 | Set C/ 7C | probe oligo | acggacgcggagCGTTGGGTTGCCAA |
| SEQ ID NO: 11 | Set D/ 7T | Invader oligo | cctgccGTGCCTCCGGAGACCGCTGGCCGGGTAGa |
| SEQ ID NO: 12 | Set D/ 7T | Invader oligo | gcggtggGTGCCTCCGGAGATCACTAGCCGGGTAGa |
| SEQ ID NO: 13 | Set D/ 7T | Invader oligo | cgggcgCGTGCCTCCGCAGGACTGCCAGCCGGGTAGa |
| SEQ ID NO: 14 | Set D/ 7T | probe oligo | acggacgcggagTGTTGGGCCGCGAAA |
| SEQ ID NO: 15 | Set E/ 3T | Invader oligo | ccGGCCCGGCCATAGAGTGGGTTAATCCGAGAAAAGACCCt |
| SEQ ID NO: 16 | Set E/ 3T | probe oligo | acggacgcggagAGTCTTTCCGGTAATTCCG |
| SEQ ID NO: 17 | Set E/ 3T | probe oligo | acggacgcggagAGTCTTCCCCGGCAGTTCCG |
| SEQ ID NO: 18 | Set F/1C | Invader oligo | ccgctcGCGGAAAGCGCCTAGCCGTGCCGTTGGTAa |
| SEQ ID NO: 19 | Set F/1C | probe oligo | acggacgcggagCGAGTGCCGTCGCGGCCTCC |
| SEQ ID NO: 20 | Set G/ 2C | Invader oligo | caggtcccgTCCAAGGAAGGATCCGGTCATCCCGCt |
| SEQ ID NO: 21 | Set G/ 2C | Invader oligo | caggtcccgTCCAAGGAAGGATCCGGTCACCCCAGCt |
| SEQ ID NO: 22 | Set G/ 2C | probe oligo | acggacgcggagGATTACGGTGTAGTCACCGG |
| SEQ ID NO: 23 | Set H/ 4 insA | Invader oligo | ggacacggaCTCCAGGGATTGAGTGGGTTTGGTCCAATc |
| SEQ ID NO: 24 | Set H/ 4 insA | probe oligo | acggacgcggagGGAAAGGGCCCGGTC |
| SEQ ID NO: 25 | Set X/ 10 all | Invader oligo | cacccggaGGACCCTGTCGTCCCGGCGATTCCGGCGTACTCGCCGGTa |
| SEQ ID NO: 26 | Set X/ 10 all | probe oligo | acggacgcggagTCCGCAGGCCACTACGGC |

SEQ ID NO: 27    RED FRET    5'-(Redmond Red™)-TCT-(Eclipse™ Dark Quencher) - AGC CGG TTT TCC GGC TGA GAC TCC GCG TCC GT-Hexandiol - 3'

SEQ ID NO: 28    FAM FRET    5'-(6-FAM)-TCT-(Eclipse™ Dark Quencher) - AGC CGG TTT TCC GGC TGA GAC CTC GGC GCG-Hexandiol-3'

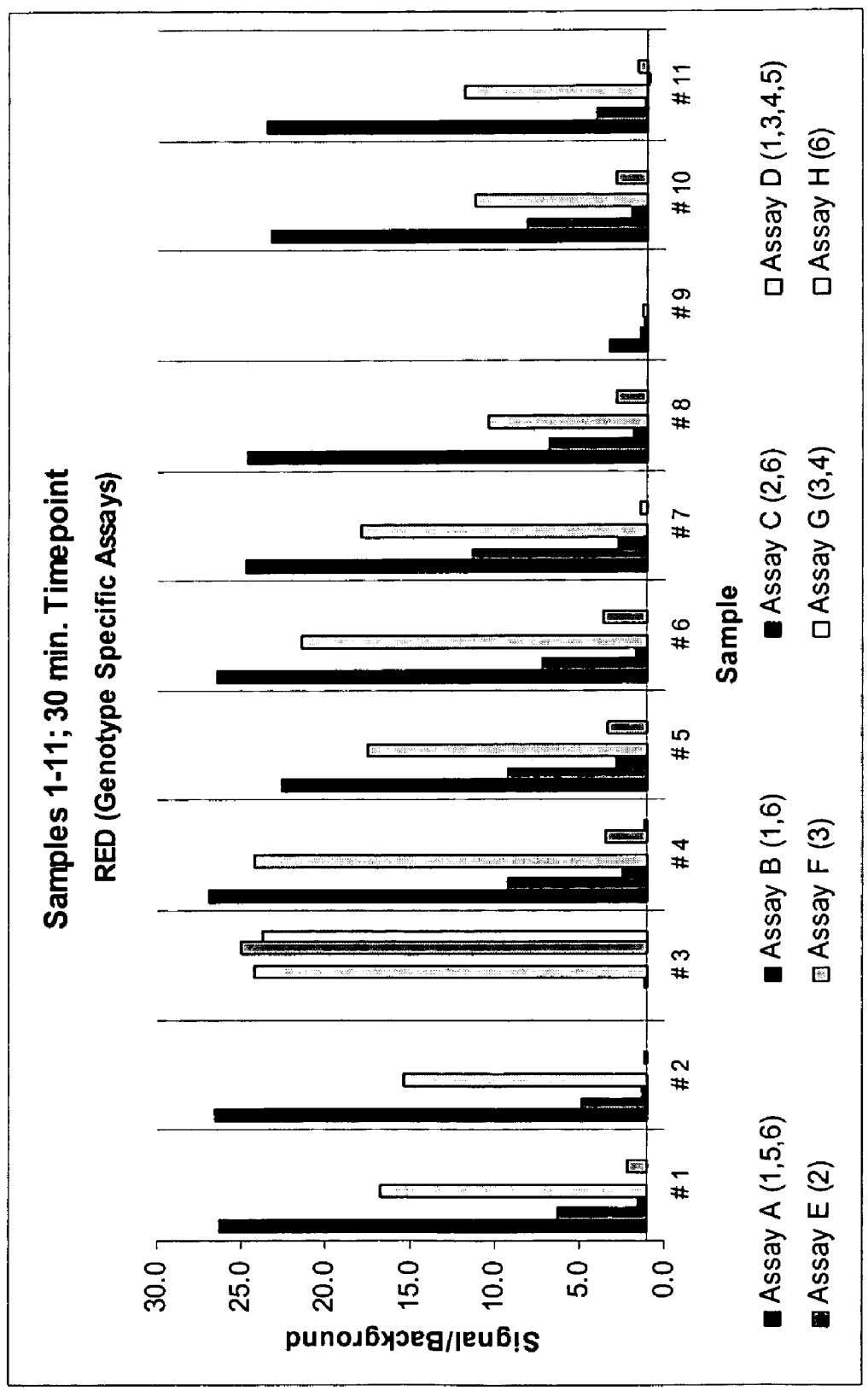

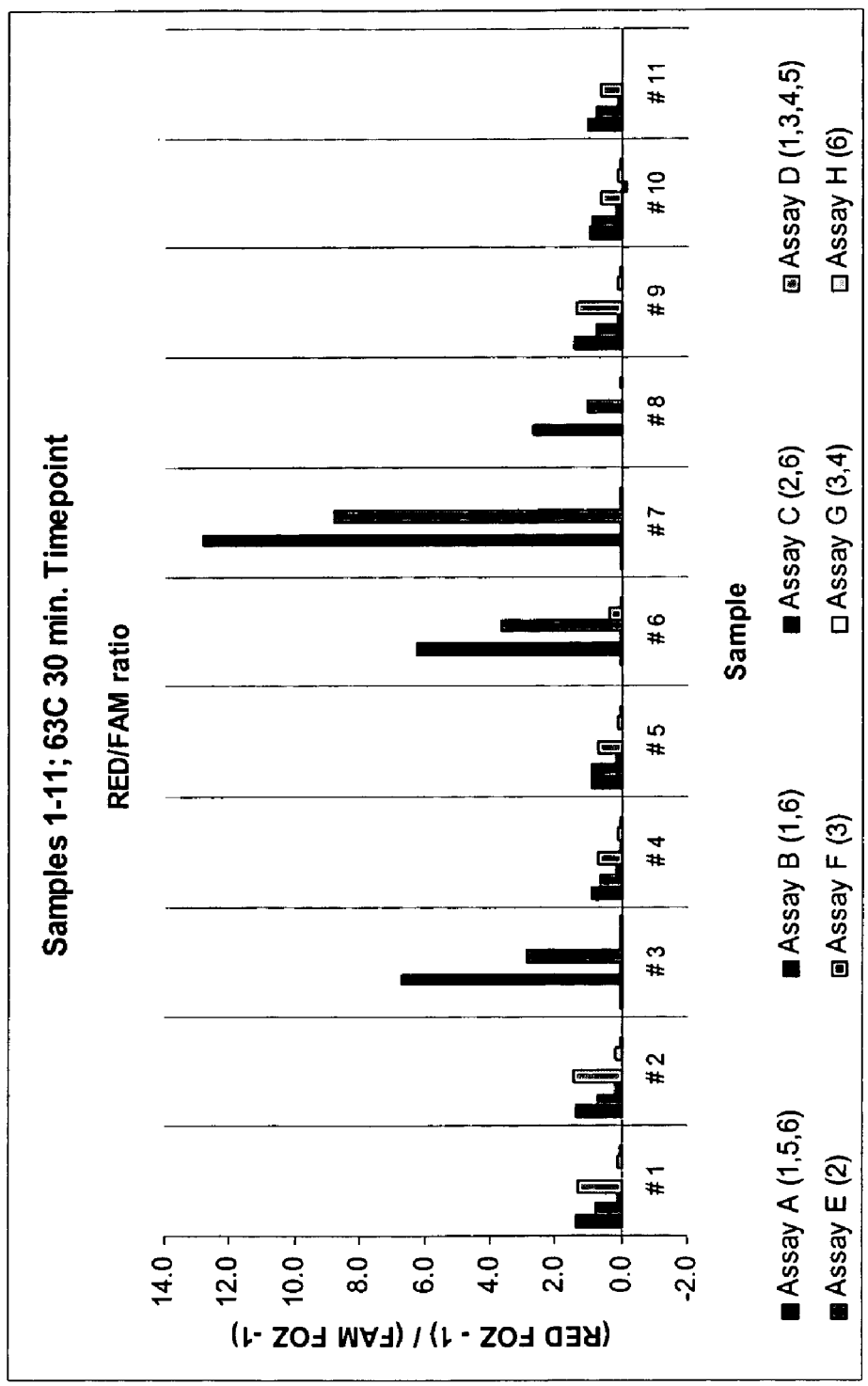

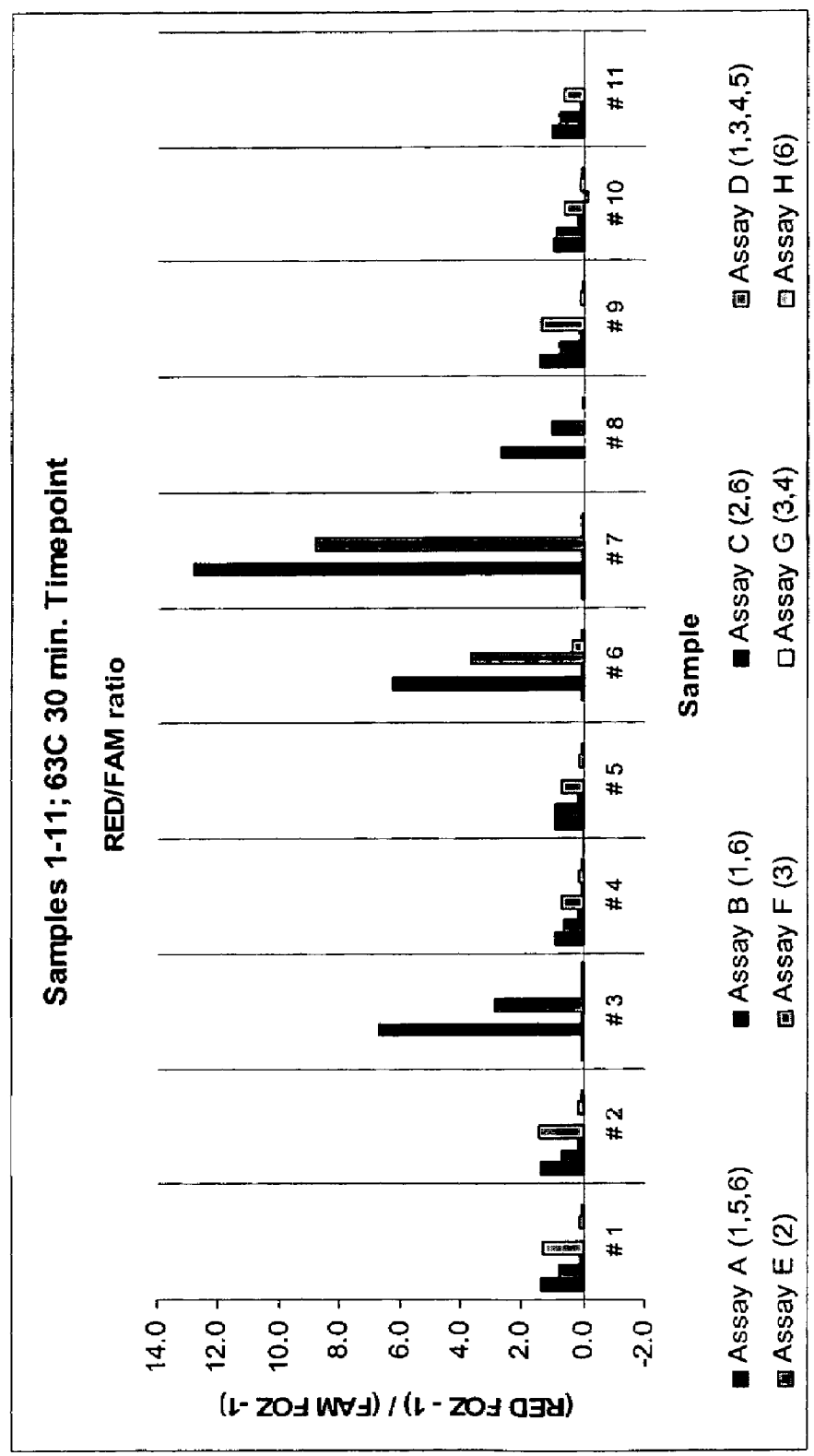

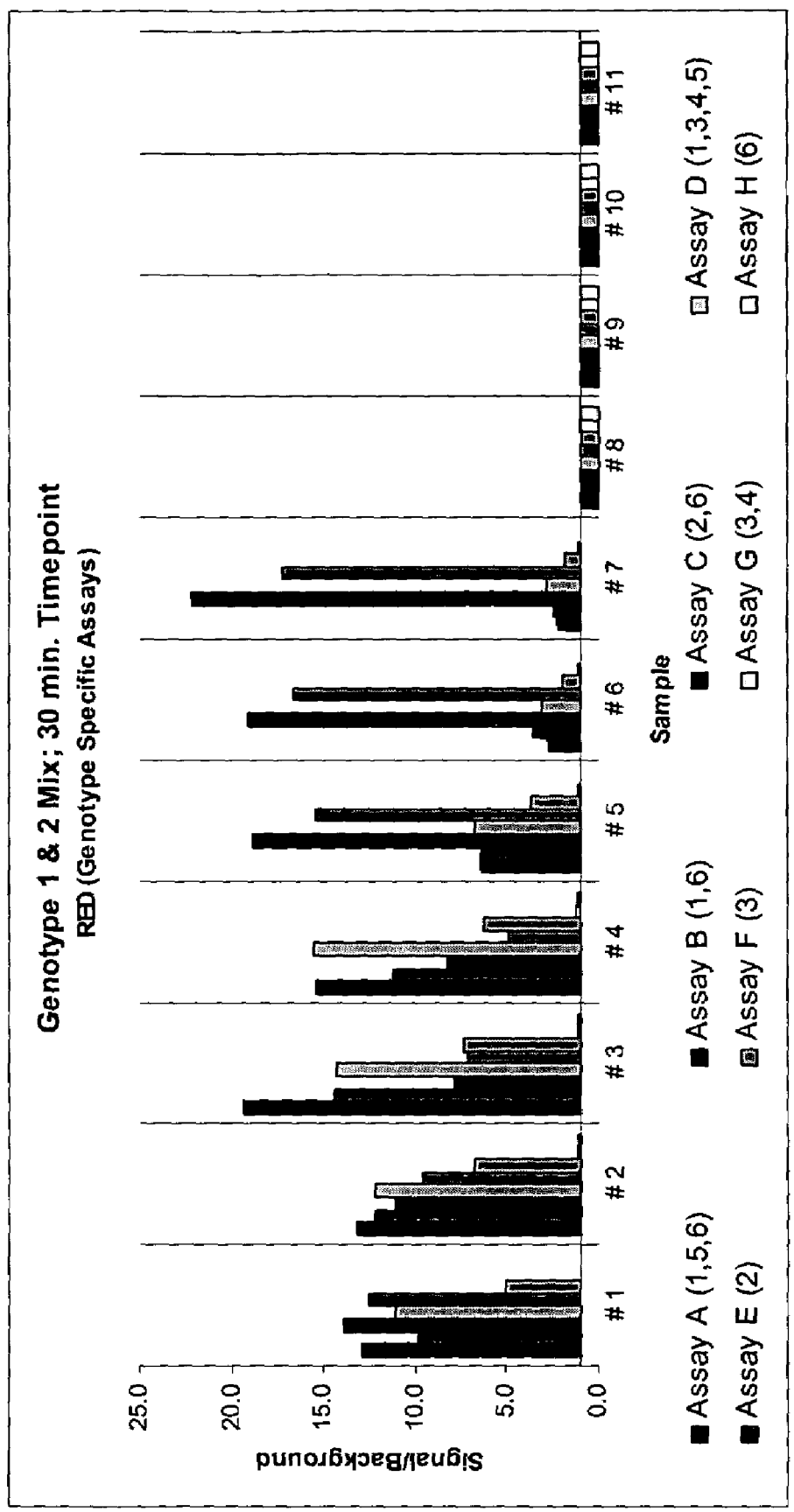

FIGURE 8

| SEQ ID NO | Assay | SNP | Oligo type | Sequence |
|---|---|---|---|---|
| SEQ ID NO: 29 | Set A/ 6G | -118 | Invader oligo | gctgcacgaaGGCTAGCGGTCTCGCAGGGGCGGCGCCTAAATa |
| SEQ ID NO: 30 | Set A/ 6G | -118 | probe oligo | acggacgcggagCTCCAGACATTGGGCGGGTT |
| SEQ ID NO: 31 | Set B/ 8T | -163 | Invader oligo | cgacctaccGGCATTGGGCGGGTTCATCCGAGAAAGGGCCCGGCCGTCCa |
| SEQ ID NO: 32 | Set B/ 8T | -163 | Invader oligo | cagccGCGGGTTCATCCGAGAAAGGGCCCGGCCGTCCa |
| SEQ ID NO: 33 | Set B/ 8T | -163 | probe oligo | acggacgcggagTGGCAATCCCGGTGCACTCACTGGTTCC |
| SEQ ID NO: 34 | Set B/ 8T | -163 | probe oligo | acggacgcggagTGCCAATTGCGGTGTA |
| SEQ ID NO: 35 | Set C/ 7C | -80 | Invader oligo | cctgccGTGCCTCCGCAGGACTGCCAGCCGGGTAGa |
| SEQ ID NO: 36 | Set C/ 7C | -80 | probe oligo | tccgcgcgtccCGTTGAGTTGCGGAAGGTCTTGTGG |
| SEQ ID NO: 37 | Set D/ 7T | -80 | Invader oligo | gcggtggGTGCCCCTGCGAGATTGCTAGCTGAGTAGa |
| SEQ ID NO: 38 | Set D/ 7T | -80 | Invader oligo | gcggtggGTGCCTCCGCTAGACCACTAGCTGAGTAGa |
| SEQ ID NO: 39 | Set D/ 7T | -80 | Invader oligo | gcggtggGTGCCTCCGCTAGACCGCTAGCTGAGTAGa |
| SEQ ID NO: 40 | Set D/ 7T | -80 | Invader oligo | gcggtggGTGCCCCTGCGAGATTGCTAGCTGAGTGGa |
| SEQ ID NO: 41 | Set D/ 7T | -80 | Invader oligo | cctgccGTGCCTCCGCAGGACTGCCAGCCGGGTAGa |
| SEQ ID NO: 42 | Set D/ 7T | -80 | probe oligo | acggacgcggagTGTTGAGTCGCGGAAGGTCTTGTGG |
| SEQ ID NO: 43 | Set D/ 7T | -80 | probe oligo | acggacgcggagTATTGGGCCGCGAAA |
| SEQ ID NO: 44 | Set E/ 3T | -155 | Invader oligo | cgcgccCCCAAAGTGGCCGGACATAGGGTGGGTTCATCCGAGAAGGGACCCt |
| SEQ ID NO: 45 | Set E/ 3T | -155 | probe oligo | acggacgcggagAGTCTTTCCGGTAATTCCG |
| SEQ ID NO: 46 | Set E/ 3T | -155 | probe oligo | acggacgcggagAGTCTTTCCGGCAGTTCCGGT |
| SEQ ID NO: 47 | Set E/ 3T | -155 | probe oligo | acggacgcggagAGTCTTCTCGGCAGTTCCGGT |
| SEQ ID NO: 48 | Set F/1C | -245 | Invader oligo | ccgctcGCGGAAAGCGCCTAGCCGTGGCGTTGGTAa |
| SEQ ID NO: 49 | Set F/1C | -245 | probe oligo | acggacgcggagCGAGTGGGCGAACGGCCT |
| SEQ ID NO: 50 | Set F/1C | -245 | probe oligo | acggacgcggagCGAGTGGCCGTGCGGCCT |
| SEQ ID NO: 51 | Set G/ 2C | -167 | Invader oligo | ggcgtcCGGGTTGCTCCAGGAAAGGGCCCGGTCCCCCGGCt |
| SEQ ID NO: 52 | Set G/ 2C | -167 | probe oligo | ggcgtcCGGGTTGCTCCAGGAAAGGGCCCGGTCCCCCCAGCt |
| SEQ ID NO: 53 | Set G/ 2C | -167 | probe oligo | ggcgtcCGGGTTGCTCCAGGAAAGGGCCCGGTCCTCCTGGCt |
| SEQ ID NO: 54 | Set G/ 2C | -167 | Invader oligo | ggcgtcCGGGTTGCTCCAGGAAAAGGGCCCGGTCCTCCCGGCt |
| SEQ ID NO: 55 | Set G/ 2C | -167 | probe oligo | acggacgcggagGATTACGGTGGACTCACC |
| SEQ ID NO: 56 | Set H/ 4 insA | -144 | Invader oligo | ggcgtcATCCCAGGCAGTGAGAGGGTTTGGTCCAATc |
| SEQ ID NO: 57 | Set H/ 4 insA | -144 | probe oligo | acgacgcggagGGAAAGGGCCCGGTC |
| SEQ ID NO: 58 | Set XI/ 11 all | -204 | Invader oligo | aaccgggCCGGTGTCGCCGGTTCGGCAGACCGCTATGc |
| SEQ ID NO: 59 | Set XI/ 11 all | -204 | probe oligo | cgcgccgaggGCTCTCTCGGGAGG |

FIGURE 8

| | | |
|---|---|---|
| SEQ ID NO: 60 | RED FRET | 5'-(Redmond Red™)-TCT-(Eclipse™ Dark Quencher) - AGC CGG TTT TCC GGC TGA GAC TCC GCG TCC GT-Hexandiol -3' |
| SEQ ID NO: 61 | FAM FRET | 5'-(6-FAM)-TCT-(Eclipse™ Dark Quencher) - AGC CGG TTT TCC GGC TGA GAC CTC GGC GCG-Hexandiol-3' |
| SEQ ID NO: 62 | RED FRET | 5'-Y-tct-X-tcg-gcc-ttt-tgg-ccg-aga-gag-gac-gcg-cgg-a-hex-3' |
| SEQ ID NO: 63 | Set C/7C -80 probe oligo | tccgcgcgtccCGTTGAGTTGCGGACGGTCTTGTG |

HCV 5' UTR Genotype Consensus Sequences

DETERMINATION OF HEPATITIS C VIRUS GENOTYPE

The present application claims priority to U.S. Provisional Application Ser. No. 60/534,618, filed Jan. 7, 2004 and to U.S. Provisional Application Ser. No. 60/563,629, filed Apr. 20, 2004, both of which are herein incorporated by reference in their entireties.

FIELD OF THE INVENTION

The present invention provides methods and composition related to nucleic acid detection assays for use in basic research, clinical research, and for the development of clinical detection assays. In particular, the present invention provides methods for determining the genotype of Hepatitis C Virus.

BACKGROUND

Hepatitis C Virus (HCV) accounts for nearly all cases of non-A, non-B hepatitis (NANBH) (Choo, Q.-L., et al., Proc. Natl. Acad. Sci. USA 88: 2451-2455 (1988)) and is a persistent health threat worldwide, with more than one million new cases reported annually (Zein, N. N. Clin. Micro. Rev. 13: 223-235 (2000)). HCV infection is almost always chronic and persistent. The most severe consequences of HCV infection are chronic liver disease and death, and HCV infection is the primary impetus for liver transplantation in the US (Zein, supra).

HCV is a positive strand single-stranded RNA virus approximately 10 kb long belonging to the Flaviviridae family (Zein, supra). There is considerable heterogeneity among isolates found in different geographic regions. These differences have been classified into multiple genotypes and subtypes. Although various different criteria have been used to characterize these genotypes, two principal modes of classification have been adopted. The more widely used of these was created by Peter Simmonds and uses Arabic numerals to denote different genotypes and latin letters for subtypes, e.g. type 1a, 1b, 2a, etc. (reviewed in Simmonds, P. Hepatology. February; 21(2):570-83 (1995) and Simmonds, P. J Hepatol.; 31 Suppl 1:54-60 (1999)). According to this system, genotypes 1-3 are the prevalent types found in North America, Europe, and Japan, and the remaining types are found at various frequencies in parts of Asia and Africa. Thus in some instances HCV genotype may be of epidemiological importance, for example in determining the etiology of infection.

Efforts have been undertaken to elucidate the clinical significance of different genotypes. Some studies suggest that infections of type 1, in particular type 1b, may be associated with more severe disease and earlier recurrence (Zein, N. N. et al., Liver Transplant. Surg. 1: 354-357 (1995); Gordon et al., Transplantation 63: 1419-1423 (1997)). Certain studies have also indicated that genotypes other than type 1 (e.g. 1a or 1b) may respond more favorably to various treatments, e.g. interferon (McHutchison, J. G., et al., N. Engl. J. Med., 339: 1485-1492 (1998)). It has been suggested that determination of HCV genotype in combination with other diagnostic markers, such as viral load, may be of value in arriving at disease prognoses (Zein, N. N. supra), and determining the course of treatment (National Institutes of Health Consensus Development Conference Statement; Management of Hepatitis C: 2002; Jun. 10-11, 2002).

Different regions of the HCV genome have been used to determine genotype. The HCV genome includes relatively conserved regions, such as the 5' and 3' untranslated regions (UTR), variable regions (e.g. E1 and non-structural (NS) 5B), as well as hypervariable regions such as those encoding the envelope proteins (Halfon, P. CLI, April 2002). Studies have been carried out to correlate the presence of particular sequences in the conserved regions with sequences in the variable regions, in particular the NS-5B (Stuyver, L., et al., J. Clin. Micro., 34: 2259-2266 (1996)). As a result of such studies, genotyping assays based on conserved regions, particularly the 5' UTR, have been developed to simplify the task of identifying which viral type or types are present in a specimen. Given the existence of commercially available viral load assays that rely on amplifying all or part of the 5' UTR, the ability to determine HCV genotype based on discrete sequence differences in this conserved region presents a convenient means of obtaining extensive diagnostic information from a single amplified nucleic acid, e.g. a RT-PCR or Transcription Mediated Amplification (TMA) amplicon.

Various molecular biological methods have been applied to the task of determining HCV genotype using the 5' UTR. These include reverse dot-blot analysis (e.g. Inno LIPA, Innogenetics, Ghent, Belgium, as described in Stuyver, L. et al., J Clin Microbiol. 1996 September; 34(9):2259-66, U.S. Pat. No. 6,495,670 and related U.S. and international patents and pending applications; direct DNA sequencing (e.g. TRUEGENE HCV 5'NC genotyping kit, Bayer Diagnostics, Berkeley, Calif., as described in Germer, J. J. et al. J Clin Microbiol. 2003 October; 41(10):4855-7), and pyrosequencing (Pyrosequencing AB, Uppsala, Sweden, as described in U.S. Pat. No. 6,258,568 and related U.S. and international patents and pending applications).

In addition to these molecular methods, serological methods for determining genotype have been introduced, e.g. the RIBA SIA test (Chiron Corp., Emeryville, Calif.) and the Murex HCV serotyping enzyme immune assay (Murex Diagnostics Ltd, Dartford, UK). Some studies indicate that serologic typing may be limited in terms of specificity and sensitivity (Zein, supra).

Therefore, there exists a need for a rapid, sensitive, accurate, and homogeneous method for accurately determining HCV genotype in a clinical sample, e.g. blood or blood fraction, without the need for electrophoretic or dot-blot techniques. Given the current reliance on molecular methods, it is likely that there will be an ongoing and increasing need for such scalable and automatable methods of determining HCV genotype.

SUMMARY OF THE INVENTION

The present invention provides compositions and methods for the determination of Hepatitis C virus (HCV) genotype. More particularly, the present invention provides compositions, methods and kits for using invasive cleavage structure assays (e.g. the INVADER assay) to screen nucleic acid samples containing HCV sequences, e.g., from patients, to identify the genotype of the virus present. The present invention may be used to detect single viral infections or mixed infections comprised of more than one HCV genotype.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ29 polymerase (as described, e.g., in U.S. Pat. Nos. 5,198,543 and 5,001,050, each herein incorporated by reference in their entireties for all purposes) in combination with exonuclease-resistant random primers, such as hexamers.

The method is not limited by the nature of the target nucleic acid. In some embodiments, the target nucleic acid is single stranded or double stranded DNA or RNA. In some embodiments, double stranded nucleic acid is rendered single stranded (e.g., by heat) prior to formation of the cleavage structure. In some embodiments, the source of target nucleic acid comprises a sample containing genomic DNA. Samples include, but are not limited to, tissue sections, blood, blood fractions (e.g. plasma, serum) saliva, cerebral spinal fluid, pleural fluid, milk, lymph, sputum and semen.

In some embodiments, the target nucleic acid comprises genomic DNA or mRNA. In other embodiments, the target nucleic acid comprises synthetic DNA or RNA. In some preferred embodiments, synthetic DNA or RNA within a sample is created using a purified polymerase. In some preferred embodiments, creation of synthetic DNA using a purified polymerase comprises the use of PCR. In some particularly preferred embodiments, the synthetic DNA created comprises all or a portion of the 5' UTR of the HCV genome. In some preferred embodiments, creation of synthetic DNA is accomplished by using a purified reverse transcriptase to generate a cDNA prior to PCR. In some particularly preferred embodiments such RT-PCR is carried out with commercial kits such as COBAS AMPLICOR or COBAS TAQMAN (Roche Molecular Systems). The method is not limited to a particular region of the HCV genome. In some preferred embodiments, the oligonucleotides of the present invention are directed to nucleotides present in the 5' UTR. In other embodiments, alternative regions amenable to genotype analysis, e.g. NS-5A, NS-5B, the core region, or the 3' UTR may be detected. In some preferred embodiments, creation of synthetic DNA comprises use of the methods and compositions for amplification using RNA-DNA composite primers (e.g., as disclosed in U.S. Pat. No. 6,251,639, herein incorporated by reference in its entirety). In other preferred embodiments, creation of synthetic DNA using a purified DNA polymerase suitable for use with the methods of the present invention comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises amplification using nucleic acids comprising loop-forming sequences, e.g., as described in U.S. Pat. No. 6,410,278, herein incorporated by reference in its entirety. In other embodiments, RNA polymerase is used to generate an RNA amplicon, e.g. through Transcription Mediated Amplification (TMA) as in U.S. Pat. No. 5,554,516 and related patents and pending applications, herein incorporated by reference.

The HCV genotyping assays provided in the present invention may find use in combination with detection assays that include, but are not limited to, enzyme mismatch cleavage methods (e.g., Variagenics, U.S. Pat. Nos. 6,110,684, 5,958, 692, 5,851,770, herein incorporated by reference in their entireties); polymerase chain reaction; branched hybridization methods (e.g., Chiron, U.S. Pat. Nos. 5,849,481, 5,710, 264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

In some embodiments, the present invention provides kits or compositions comprising a non-amplified oligonucleotide detection assay configured for detecting at least one HCV genotype sequence. In other embodiments, the non-amplified oligonucleotide detection assay comprises first and second oligonucleotides configured to form an invasive cleavage structure (e.g. an INVADER assay) in combination with a target sequence comprising said at least one HCV genotype sequence. In particular embodiments, the first oligonucleotide comprises a 5' portion and a 3' portion, wherein the 3' portion is configured to hybridize to the target sequence, and wherein the 5' portion is configured to not hybridize to the target sequence. In other embodiments, the second oligonucleotide comprises a 5' portion and a 3' portion, wherein the 5' portion is configured to hybridize to the target sequence, and wherein the 3' portion is configured to not hybridize to the target sequence.

In some embodiments, the detected HCV 5' UTR sequences are any of those found in Genbank, NCBI, Hepatitis Virus Database or variants thereof. It is understood that sequences will diverge over time and that other HCV varieties, now known, or later discovered are readily adaptable to the methods and composition of the present invention, per the description herein.

In certain embodiments, the oligonucleotide detection assays are selected from sequencing assays, polymerase chain reaction assays, hybridization assays, hybridization assays employing a probe complementary to a mutation, microarray assays, bead array assays, primer extension assays, enzyme mismatch cleavage assays, branched hybridization assays, rolling circle replication assays, NASBA assays, molecular beacon assays, cycling probe assays, ligase chain reaction assays, invasive cleavage structure assays, ARMS assays, and sandwich hybridization assays.

In some embodiments, the present invention provides methods of determining HCV genotype, comprising; a) providing; i) a sample from a subject; ii) a means of generating double-stranded DNA from the HCV genome; iii) a composition comprising an oligonucleotide detection assay (e.g. as described herein); and b) contacting said sample with said composition such that the presence or absence of at least one HCV genotype is determined. In some embodiments, the sample is a blood sample or blood fraction sample (e.g. plasma, serum, red blood cells), mouth swab sample, e.g. buccal cells, cervical swab, stool, saliva sample, or other biological fluid sample from the subject such as pleural fluid, sputum, urine, amnion, cerebrospinal fluid, or sweat.

In still other embodiments, the present invention also provides a method for genotyping a sample containing HCV comprising the steps of: a) detecting one or more (e.g., 2 or more, 5 or more) single nucleotide polymorphisms in nucleic acid amplified from the 5' UTR of said HCV sample; b) generating a 5' UTR genotype profile based on the information derived from step a; and, in some embodiments, comparing said 5' UTR genotype profile to a predetermined HCV information matrix, such that an HCV genotype of said subject is determined. In some embodiments, the predetermined HCV information matrix is stored in a computer memory. In some preferred embodiments, the method further comprises the step of using said HCV genotype in selecting a therapy for a subject (e.g., selecting an appropriate drug, selecting an appropriate dose of drug, avoiding certain drugs, continuing administration of a certain drug for a certain number of days, etc.).

In some embodiments, the present invention provides compositions comprising an invasive cleavage detection assay, wherein the invasive cleavage detection assay is configured for detecting a single nucleotide polymorphism in a position of a 5' UTR sequence of HCV selected from the group consisting of: −245, −167, −163, −155, −144, −118, and −80.

In other embodiments, the present invention provides methods comprising; a) providing; i) a sample from a subject, wherein the sample is suspected of containing HCV, and ii) a composition comprising an invasive cleavage detection assay, wherein the invasive cleavage detection assay is configured for detecting a single nucleotide polymorphism in a position of a 5' UTR sequence of HCV selected from the group consisting of: −245, −167, −163, −155, −144, −118, and −80; and b) contacting the composition with the sample under conditions such that at least one of the single nucleotide polymorphisms is detected. In certain embodiments, the contacting determines the identity of the base as the position (e.g. "G," "C," "A," or "T"). In other embodiments, the sample is from a subject.

In certain embodiments, the invasive cleavage assay comprises a first oligonucleotide, wherein the first oligonucleotide comprises a 5' portion and a 3' portion, wherein the 3' portion is configured to hybridize to the 5' UTR sequence of HCV, and wherein the 5' portion is configured to not hybridize to the 5' UTR sequence of HCV. In other embodiments, the first oligonucleotide is a sequence selected from the group consisting of SEQ ID NOs:2-4, 7, 8, 10, 14, 16, 17, 19, 22, 24, 26, 30, 33, 34, 36, 42, 43, 45-47, 49, 50, 55, 57, 59, and 63.

In particular embodiments, the invasive cleavage assay comprises a second oligonucleotide, wherein the second oligonucleotide comprises a 5' portion and a 3' portion, wherein the 5' portion is configured to hybridize to the 5' UTR sequence of HCV, and wherein the 3' portion is configured to not hybridize to the 5' UTR sequence of HCV. In other embodiments, the second oligonucleotide is a sequence selected from the group consisting of SEQ ID NOs:1, 5, 6, 9, 11-13, 15, 18, 20, 21, 23, 25, 29, 31, 32, 35, 37-41, 44, 48, 51-54, 56, and 58.

In some embodiments, the 5' UTR sequence of HCV comprises RNA (e.g. the RNA of the HCV virus is detected without converting into cDNA). In certain embodiments, the 5' UTR sequence of HCV comprises DNA (e.g. the RNA of the HCV is converted into cDNA prior to detection).

In some embodiments, the present invention provides methods comprising; a) providing; i) a sample from a subject, wherein the sample is suspected of containing hepatitis C virus, and ii) a plurality of oligonucleotide detection assays, wherein each of the oligonucleotide detections assays is configured for detecting a single nucleotide polymorphisms in a 5' UTR sequence of HCV, and b) contacting the sample with the plurality of oligonucleotide detection assays under conditions such that at least partial genotype information for each of the single nucleotide polymorphisms is determined thereby generating a 5' UTR genotype profile, wherein the 5' UTR genotype profile is sufficient to genotype the hepatitis C virus.

In certain embodiments, the method further comprises c) genotyping the hepatitis C virus based on the 5' UTR genotype profile as Genotype I, II, III, IV, V, or VI. In preferred embodiments, the genotyping classifies the hepatitis C virus as being Genotype I, IV or V. In other embodiments, the plurality of oligonucleotide detection assays comprise invasive cleavage structure type assays. In particular embodiments, the plurality of oligonucleotide detections assays comprise at least one of the following types of assays: a TAQMAN assay, a sequencing assay, a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a rolling circle replication assay, a NASBA assay, a molecular beacon assay, a cycling probe assay, a ligase chain reaction assay, and a sandwich hybridization assay. In particular embodiments, the plurality of oligonucleotide detection assays comprise non-amplified oligonucleotide type detection assays.

In some embodiments, at least one of the plurality of the oligonucleotide detection assays comprises a first oligonucleotide, wherein the first oligonucleotide comprises a 5' portion and a 3' portion, wherein the 3' portion is configured to hybridize to the 5' UTR sequence of HCV, and wherein the 5' portion is configured to not hybridize to the 5' UTR sequence of HCV. In other embodiments, at least one of the plurality of the oligonucleotide detection assays comprises a second oligonucleotide, wherein the second oligonucleotide comprises a 5' portion and a 3' portion, wherein the 5' portion is configured to hybridize to the 5' UTR sequence of HCV, and wherein the 3' portion is configured to not hybridize to the 5' UTR sequence of HCV. In additional embodiments, the plurality of oligonucleotide detection assays comprise oligonucleotides that contain at least one mismatch when hybridized with the 5' UTR sequence.

In other embodiments, the plurality of oligonucleotide detection assays comprises at least two oligonucleotide detection assays (e.g. 2 or 3). In further embodiments, the plurality of oligonucleotide detection assays comprises at least four oligonucleotide detection assays (e.g. 4, 5, 6, or 7). In some embodiments, the plurality of oligonucleotide detection assays comprises at least eight oligonucleotide detection assays (e.g. 8, 9 or 10).

In additional embodiments, the single nucleotide polymorphisms in the 5' UTR sequence of HCV are located in at least two of the following positions: −245, −167, −163, −155, −144, −118, and −80. In other embodiments, the 5' UTR genotype profile indicates: i) an "A" at position −163; ii) no "C" at position −144; and optionally iii) no "C" at position −167; or a "T" a position −167; and wherein the method further comprises genotyping the hepatitis C virus based on the 5' UTR genotype profile as Genotype I.

In certain embodiments, the 5' UTR genotype profile indicates: i) an "A" at position −163; ii) a "T" at position −80; and optionally iii) no "C" at position −167; or a "T" a position −167; and wherein the method further comprises genotyping the hepatitis C virus based on the 5' UTR genotype profile as Genotype I. In further embodiments, the 5' UTR genotype profile indicates: i) an "A" at position −163; ii) a "C" at position −72; and optionally iii) no "C" at position −167; or a "T" a position −167; and wherein the method further comprises genotyping the hepatitis C virus based on the 5' UTR genotype profile as Genotype I.

In other embodiments, the 5' UTR genotype profile indicates: i) a "T" at position −122; ii) no "C" at position −144; and optionally iii) no "C" at position −167; and wherein the method further comprises genotyping the hepatitis C virus based on the 5' UTR genotype profile as Genotype I. In additional embodiments, the 5' UTR genotype profile indicates: i) a "T" at position −122; ii) a "T" at position −80; and optionally iii) no "C" at position −167; and wherein the method further comprises genotyping the hepatitis C virus based on the 5' UTR genotype profile as Genotype I.

In particular embodiments, the 5' UTR genotype profile indicates: i) a "T" at position −122; ii) a "C" at position −72; and optionally iii) no "C" at position −167; and wherein the method further comprises genotyping the hepatitis C virus based on the 5' UTR genotype profile as Genotype I. In certain embodiments, the 5' UTR genotype profile indicates: i) an "A" at position −132; and optionally ii) a "G" at position −163; and wherein the method further comprises genotyping the hepatitis C virus based on the 5' UTR genotype profile as Genotype II.

In further embodiments, the 5' UTR genotype profile indicates: i) a "Y" ("C" or "T") at position −119; and optionally ii) no "C" at position −167, or a "T" at position −167; and wherein the method further comprises genotyping the hepatitis C virus based on the 5' UTR genotype profile as Genotype II. In some embodiments, the 5' UTR genotype profile indicates: i) a "T" at position −245; and ii) a "C" at position −167; and wherein the method further comprises genotyping the hepatitis C virus based on the 5' UTR genotype profile as Genotype IV.

In additional embodiments, the 5' UTR genotype profile indicates: i) a "T" at position −245; and ii) an "A" at position −118; and wherein the method further comprises genotyping the hepatitis C virus based on the 5' UTR genotype profile as Genotype IV. In certain embodiments, the 5' UTR genotype profile indicates: i) a "T" at position −167; ii) a "G" at position −163; and iii) a "C" at position −155; and wherein the method further comprises genotyping the hepatitis C virus based on the 5' UTR genotype profile as Genotype V.

In other embodiments, the 5' UTR genotype profile indicates: i) a "C" at position −122; and ii) a "G" at position −117; and wherein the method further comprises genotyping the hepatitis C virus based on the 5' UTR genotype profile as Genotype V. In particular embodiments, the 5' UTR genotype profile indicates: i) a "G" at position −117; and ii) a "C" at position −80; and wherein the method further comprises genotyping the hepatitis C virus based on the 5' UTR genotype profile as Genotype VI.

In some embodiments, the 5' UTR genotype profile indicates: i) an "A" at position −118; and ii) a "C" at position −80; and wherein the method further comprises genotyping the hepatitis C virus based on the 5' UTR genotype profile as Genotype VI. In further embodiments, the 5' UTR genotype profile indicates: i) a "T" at position −122; and ii) a "C" at position −80; and wherein the method further comprises genotyping the hepatitis C virus based on the 5' UTR genotype profile as Genotype VI. In other embodiments, the 5' UTR genotype profile indicates: i) a "T" at position −122; and ii) a "T" at position −72; and wherein the method further comprises genotyping the hepatitis C virus based on the 5' UTR genotype profile as Genotype VI.

Definitions

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components".

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In other embodiments, In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \ G+C)$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the Cleavase enzymes, the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090,606; PCT Appln. Nos WO 98/23774; WO 02/070755A2; and WO 0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

As used herein, the phrase "non-amplifying oligonucleotide detection assay" refers to a detection assay configured to detect the presence or absence of a particular polymorphism (e.g., SNP, repeat sequence, etc.) in a target sequence (e.g., genomic DNA, or amplified or other synthetic DNA), without creating copies of the target sequence. A "non-amplifying oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P"

nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein, the term "purified" or "to purify" refers to the removal of contaminants from a sample. For example, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n–1).

The term "nucleic acid sequence" as used herein refers to an oligonucleotide, nucleotide or polynucleotide, and fragments or portions thereof, and to DNA or RNA of genomic or synthetic origin which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

The phrase "5' UTR genotype profile" refers the combined results from at least two oligonucleotide detection assays configured to detect single nucleotide polymorphisms in the 5' UTR sequence of the hepatitis C virus and provides at least partial genotype information at each single nucleotide polymorphism position. A 5' UTR genotype profile does not contain sequence information from non-5' UTR HCV sequences (e.g. sequence information from coding regions). Examples of 5' UTR genotype profiles are shown for each sample in FIGS. 4, 5C, 6C and 9. In preferred embodiments, a 5' UTR genotype profile is sufficient to genotype (e.g. classify into genotype I, II, III, IV, IV, and VI) a hepatitis C virus without additional sequence information from non-5' UTR sequences of the hepatitis C virus.

As used herein, the phrase "partial genotype information" in regard to a particular 5' UTR HCV single nucleotide polymorphism means that the particular base that is detected reveals information that narrows the possible genotype of the HCV detected to between two and five of the standard six HCV genotypes (i.e. partial genotype information does not provide the exact genotype, but at a minimum excludes at least one of the six HCV genotypes, and may narrow it down to two possible genotypes). One example of an assay that provides partial genotype information is provided by Assay A (detecting position −118), where a positive result (detecting a "G") indicates the possible presence of Genotypes I, V, or VI (See position −118 in FIG. 10 which shows that only Genotypes I, V and VI have a "G" at this position). If a particular oligonucleotide detection assay provides "at least" partial genotype information, this assay at least excludes one of the six standard HCV genotypes, and may provide the exact genotype via this single nucleotide polymorphism (e.g. Assay H in FIG. 7, if detected, reveals the presence of Genotype VI; see also FIG. 10 which shows that only Genotype VI has a "C" [CA insert] at position −144/5).

DESCRIPTION OF THE DRAWINGS

FIG. 3 shows sequences of detection assay components in some embodiments of the present invention. Probes contain a hexanediol blocking group at their 3' ends. Lower case letters indicate non-complementary flaps.

FIG. 7 shows the results of invasive cleavage assays carried out on mixtures of PCR amplicons generated with COBAS AMPLICOR viral load assays designed to detect HCV sequences.

FIG. 8 shows sequences of detection assay components in some embodiments of the present invention. Probes contain a hexanediol blocking group at their 3' ends. Lower case letters indicate non-complementary flaps.

DESCRIPTION OF THE INVENTION

The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, 6,090,543, 6,348,314, and 6,458,535, WO 97/27214 WO 98/42873, Lyamichev et al., Nat. Biotech., 17:292 (1999), Hall et al., PNAS, USA, 97:8272 (2000), each of which is herein incorporated by reference in its entirety for all purposes).

The INVADER assay detects hybridization of probes to a target by enzymatic cleavage of specific structures by structure specific enzymes (see, e.g., U.S. Pat. Nos. 5,846,717; 6,090,543; 6,001,567; 5,985,557; 5,994,069; 6,090,543; 6,348,314; 6,458,535; U.S. Patent App. Nos. 20030186238 (Ser. No. 10/084,839); 20030104378A1 (Ser. No. 09/864, 636); Lyamichev et al., Nat. Biotech., 17:292 (1999), Hall et al., PNAS, USA, 97:8272 (2000), WO 97/27214 and WO 98/42873, each of which is herein incorporated by reference in its entirety for all purposes).

Figure 1:
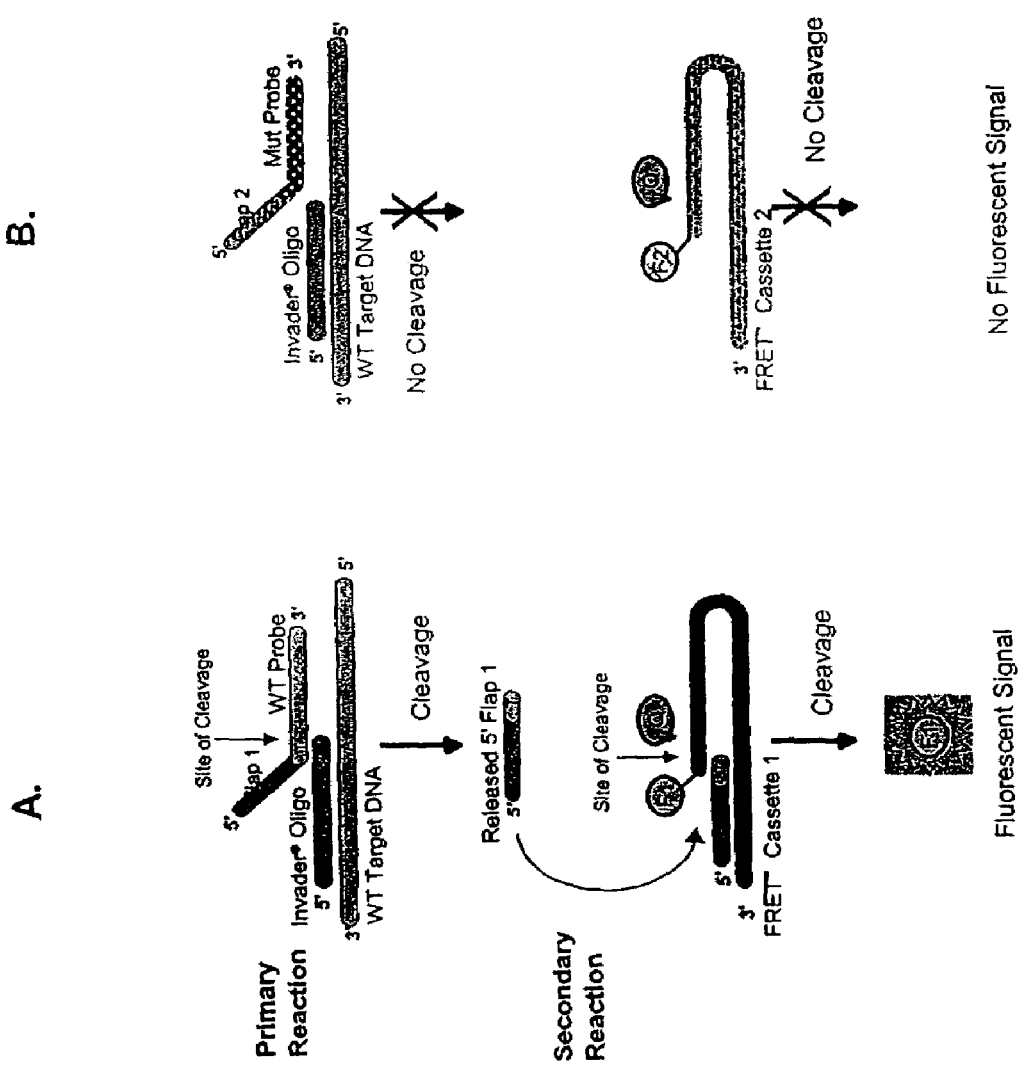
FIG. 1 shows a schematic diagram of INVADER oligonucleotides, probe oligonucleotides and FRET cassettes for detecting a two different alleles (e.g., differing by a single nucleotide) in a single reaction.

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific sequences, mutations, and SNPs in unamplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In the secondary reaction, each released 5'-flap can serve as an INVADER oligonucleotide on a fluorescence resonance energy transfer (FRET) Cassette to create another overlapping structure that is recognized and cleaved by the CLEAVASE enzyme (FIG. 1). When the FRET Cassette is cleaved, the fluorophore (F) and quencher (Q) are separated, generating detectable fluorescence signal. Similar to the initial reaction, the released 5'-flap and the FRET Cassette cycle, resulting in amplified fluorescence signal. The initial and secondary reactions run concurrently in the same well.

The biplex format of the INVADER DNA assay enables simultaneous detection of two DNA sequences in a single well. Most often, this involves detection of two variants of a particular polymorphism. The biplex format uses two different discriminatory Primary Probes, each with a unique 5'-flap, and two different FRET Cassettes, each with a spectrally distinct fluorophore. By design, the released 5'-flaps will bind only to their respective FRET Cassettes to generate a target-specific signal.

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| CLEAVASE enzyme (e.g., CLEAVASE X) | Primary Oligos |
|---|---|
| DNA Reaction Buffer 1 | INVADER Oligo |
| | FRET Cassette 1 (e.g., F) |
| | FRET Cassette 2 (e.g., R) |
| | Mutant DNA controls |
| | Wild type DNA controls |
| | "No Target" Blank control |

In some embodiments, the kits of the present invention provide the following reagents:

| CLEAVASE enzyme mix (e.g., CLEAVASE X) in 210 mM MgCl$_2$, 40% glycerol | Mutation Mixes containing the following constituents in 25 mM MOPS, pH 7.5: Primary Oligos INVADER Oligos FRET Cassette 1 (e.g., F) FRET Cassette 2 (e.g., a second F cassette) FRET Cassette 3 (e.g. R) Mutant DNA controls Internal DNA controls "No Target" Blank control |
|---|---|

Figure 2:
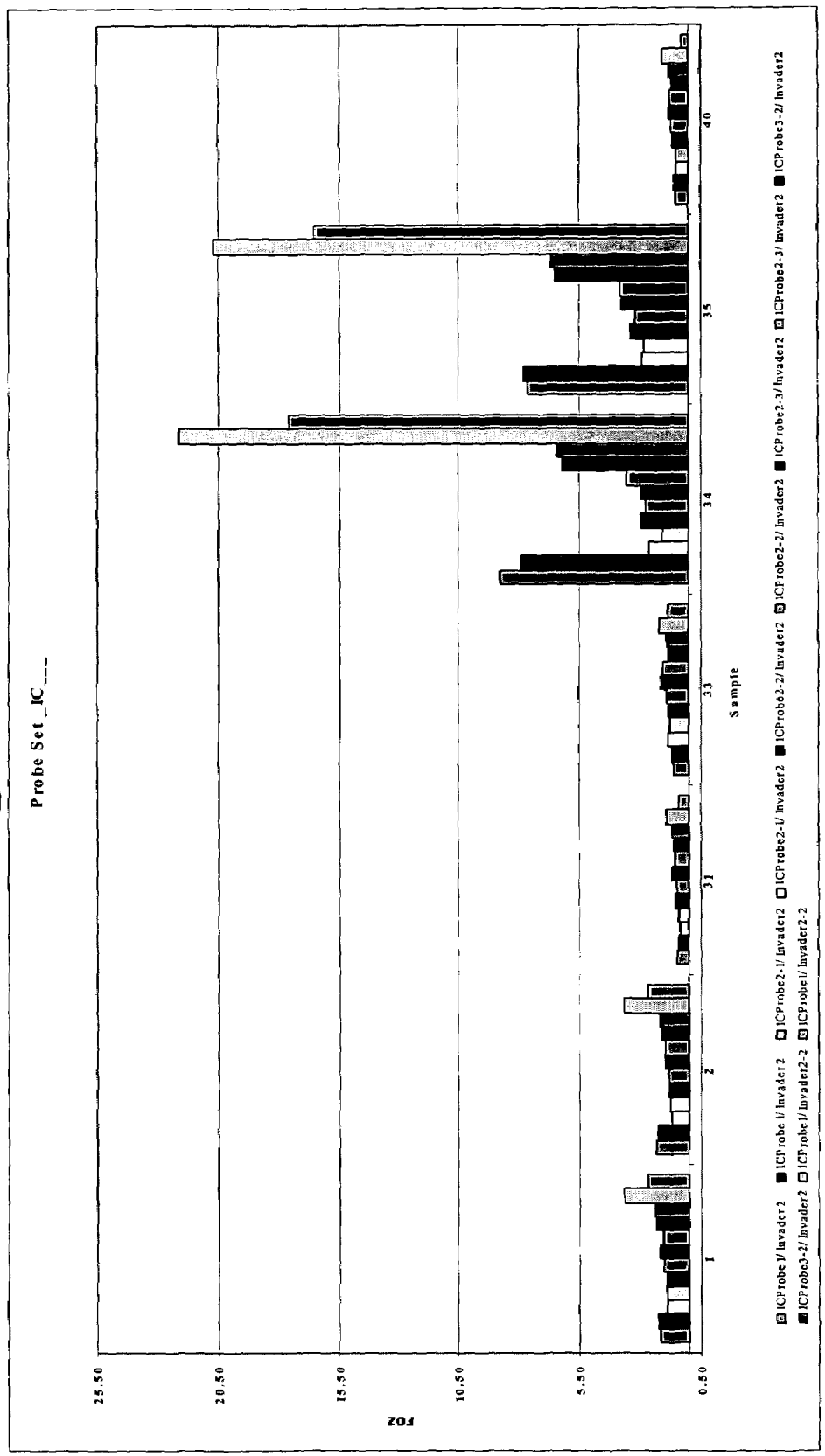
FIG. 2 shows the results of invasive cleavage assays carried out on PCR amplicons generated with COBAS AMPLICOR viral load assays designed to detect HCV sequences.

Examples of Primary Oligonucleotides, Secondary Oligonucleotides, and FRET Cassettes suitable for use with the methods of the present invention are provided in FIGS. 2, 3 and 8. While the oligonucleotides shown therein may find use in a number of the methods, and variations of the methods, of the present invention, these INVADER assay oligonucleotide sets find particular use with kits of the present invention. The oligonucleotide sets shown in FIGS. 2, 3 and 8 may be used as individual sets to detect individual target DNAs, or may be combined in biplex or multiplex reactions for the detection of two or more analytes or controls in a single reaction.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197, 557, issued Mar. 6, 2001, and in PCT application WO 98/39485, each incorporated by reference herein in their entireties for all purposes.

In some embodiments, the present invention provides methods for detecting a target sequence, comprising: providing a) a sample containing DNA amplified by extension of 3' ends in nicked double-stranded genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ29 polymerase (as described, e.g., in U.S. Pat. Nos. 5,198,543 and 5,001,050, each herein incorporated by reference in their entireties for all purposes) in combination with exonuclease-resistant random primers, such as hexamers.

In some embodiments, the present invention provides methods for detecting a target sequence, comprising: providing a) a sample containing DNA amplified by extension of multiple primers on genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some preferred embodiments, said primers are random primers. In particularly preferred embodiments, said primers are exonuclease resistant. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In certain embodiments, the present invention provides kits for assaying a pooled sample (e.g., a pooled blood sample) using INVADER detection reagents (e.g. primary probe, INVADER probe, and FRET cassette). In preferred embodiments, the kit further comprises instructions on how to perform the INVADER assay and specifically how to apply the INVADER detection assay to pooled samples from many individuals, or to "pooled" samples from many cells (e.g. from a biopsy sample) from a single subject.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, [The kinetics of oligonucleotide replacement. Luis P. Reynaldo, Alexander V. Vologodskii, Bruce P. Neri and Victor I. Lyamichev. J. Mol. Biol. 97: 511-520 (2000)], multiple probes can hybridize to the same target, allowing multiple cleavages, and the generation of multiple cleavage products.

In some embodiments, the detection assays of the present invention are designed to detect one or more HCV sequences. In some embodiments, HCV genotypes are determined by the composite results of one or more detection assays. In some preferred embodiments, two or more detection assays are carried out on each sample. In still other preferred embodiments, two or more detection assays are carried out on each sample to generate a 5' UTR genotype profile. In some embodiments, eight detection assays are used to generate a 5' UTR genotype profile. In some particularly preferred embodiments, an assay is carried out to detect a common sequence for use as an internal control assay. In still other embodiments, the present invention also provides a method for genotyping a sample containing HCV comprising the steps of: a) detecting one or more (e.g., 2 or more, 5 or more) single nucleotide polymorphisms in nucleic acid amplified from the 5' UTR of said HCV sample; b) generating a 5' UTR genotype profile based on the information derived from step a; and, in some embodiments, comparing said 5' UTR genotype profile to a predetermined HCV information matrix, such that an HCV genotype of said subject is determined. In some embodiments, the predetermined HCV information matrix is stored in a computer memory. In some preferred embodiments, the method further comprises the step of using said HCV genotype in selecting a therapy for a subject (e.g., selecting an appropriate drug, selecting an appropriate dose of drug, avoiding certain drugs, continuing administration of a certain drug for a certain number of days, etc.).

In some embodiments, the oligonucleotides used in the detection assay are perfectly complementary to the intended HCV target sequence. In other embodiments, the oligonucleotides contain one or more mismatches to the HCV target sequence of interest. Mismatches find multiple uses, including, but not limited to, the ability to reduce hybridization efficiency (which may be desired in some detection assay formats), the ability to add degeneracy (e.g., to detect two or more strains or variants), and the ability to compensate for sequence variation that may be in a sample. In some embodiments, where variation at a particular nucleotide position is identified in some members of a tested population, multiple oligonucleotides are provided that differ in sequence at the position so that each variant within the population is detected. Exemplary detection assay components for use in invasive cleavage assays are provided in the Example section below for certain genotypes of HCV. It is contemplated that the designs of these probe sets (e.g., the oligonucleotides and/or their sequences) may be adapted for use in RNA detection assays, using the guidelines for reaction design and optimization provided herein.

In some embodiments, a kit of the present invention provides a list of additional components (e.g., reagents, supplies, and/or equipment) to be supplied by a user in order to perform the methods of the invention. For example, and without intending to limit such additional component lists to any particular components, one embodiment of such a list comprises the following:

Clear CHILLOUT-14 liquid wax (MJ Research) or RNase-free, optical grade mineral oil (Sigma, Cat. No. M-5904)

96-well polypropylene microplate (MJ Research, Cat. No. MSP-9601)

Sterile 1.5-ml or 2.0-ml microcentrifuge tubes

Sterile, DNase/RNase free disposable aerosol barrier pipet tips

Multichannel pipets (0.5-10 µl, 2.5-20 µl)

Thermal cycler or other heat source (e.g., lab oven or heating block).

Miscellaneous laboratory equipment (tube racks, micropipetors, multichannel pipet, microcentrifuge, vortex mixer).

Fluorescence microplate reader (a preferred plate reader is top-reading, equipped with light filters have the following characteristics:

| Excitation (Wavelength/Bandwidth) | Emission (Wavelength/Bandwidth) |
| --- | --- |
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

Sterile 8-tube strip or microplate (optional)

Disposable plastic trough (optional)

Plate sealing tape (optional)

In some embodiments, a kit of the present invention provides a list of required components to be supplied by a user to facilitate performance of the methods of the invention for which multiple alternatives are acceptable (e.g. sample preparation kits). For example, and without intending to limit such optional components lists to any particular components, one embodiment of such a list comprises the following:

QIAGEN QIamp® Blood Kit

Gentra Systems PUREGENE™ Kit

Gentra Systems GENERATION® Products

In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions). By way of example, and without intending to limit such protocols to any particular content or format, kits of the present invention may comprise the following protocol:

I. Detailed DNA Biplex Invader Assay Protocol
1. Determine the number of samples and controls to be tested.
2. Plan the microplate layout for each experimental run (e.g., samples, controls). Inclusion of a No Target Control (tRNA Carrier in buffered, nuclease-free water) is required for a valid result.
3. Prepare the INVADER DNA Assay Reaction Mix for the biplex assay format. To calculate the volumes of reaction components needed for the assay (X Volume), multiply the total number of reactions (samples and controls) by 1.25 [X Volume (µl)=# reactions×1.25]. Vortex the INVADER DNA Assay Reaction Mix briefly after the last reagent addition to mix thoroughly.

INVADER DNA Assay Reaction Mix

| Biplex Assay Format | | |
| --- | --- | --- |
| Reaction Components | 1X Volume | _X Volume |
| DNA Reaction Buffer 1 | 5.0 µl | |
| FRET F Cassette | 1.0 µl | |
| FRET R Cassette | 1.0 µl | |
| Primary Probes | 1.0 µl | |
| INVADER Oligo | 1.0 µl | |
| CLEAVASE enzyme | 1.0 µl | |
| Total Mix Volume (1X) | 10.0 µl | |

4. Add 10 µl of each control or DNA sample (≧150 ng DNA) to the appropriate well and mix by pipetting up and down 1-2 times. Overlay each reaction with 20 µl of clear CHILLOUT or mineral oil. Seal microplate with Thermaseal well tape (optional).
5. Incubate reactions for 10 minutes at 98° C. in a thermal cycler or oven.
6. Lower the temperature to 63° C. in the thermal cycler or transfer the plate to a 63° C. heat block, then add 10 µl of the INVADER® DNA Assay Reaction Mix to each well and mix well by pipetting up and down 3 to 5 times. An 8-tube strip or microplate may be used to facilitate addition of the INVADER® DNA Assay Reaction Mix using a multichannel pipet. When adding the INVADER® DNA Assay Reaction Mix, be sure to add the mix below the level of the mineral oil or Chill-out™ 14 liquid wax.
7. Cover the microplate with plate sealing tape (optional) and incubate at 63° C. for 4 hours.
8. After the 4-hour incubation, place the microplate in the plate holder of the fluorescence plate reader. Remove plate sealing tape, if used.
9. Read the plate at the two different wavelength settings (The dye corresponding to the WT and Mut signal is not necessarily the same for all biplex assays).
10. The gain should be set so that Control 4 reads between 100 and 200 for each scan. The Control 4 values do not have to be identical for the F and R dye scans.
    NOTE: Remove the microplate seal before reading the microplate.
    This procedure enables collection of multiple data sets to extend the assay's dynamic range. During the secondary INVADER reaction, read the microplate directly in a top-reading fluorescence microplate reader.
    NOTE: Because the optimal gain setting can vary between instruments, adjust the gain as needed to give the best signal/background ratio (sample raw signal divided by the No Target Control signal) or No Target Control sample readings of ~100 RFUs. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

Calculation of Ratios and Guidelines for Interpretation

In some embodiments of a kit, guidelines for using the ratios of the two fluorescent signals to determine a genotype are provided. For example, for each allele of a given polymorphism, the net signal/background, or Net Fold Over Zero (FOZ −1), values may be calculated as follows for the signal obtained with each dye:

$$FOZ = \frac{\text{Raw counts from sample}}{\text{Raw counts from No Target Blank}}$$

The two FOZ values (i.e. internal control and genotype-specific read) for each sample were used to calculate the assay output ratio as follows:

$$\text{Ratio} = \frac{(\text{Net Genotype-specific } FOZ)}{(\text{Internal Control } FOZ)}$$

where Net FOZ=FOZ −1

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections to intended to aid the user in resolving or avoiding such problems.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); mol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); and ° C. (degrees Centigrade).

Example 1

Design of Oligonucleotides to Detect Multiple HCV Strains

The objective of these experiments was to arrive at oligonucleotide designs suitable for use in INVADER assays to detect particular sequences in the 5' UTR of HCV. As a first step, HCV DNA sequences were obtained from Genbank (NCBI) and the Hepatitis Virus Database (found at: s2as02.genes.nig.ac.jp) and aligned using Clustal W (DNA Star, Madison, Wis.). Regions that combined suitable sequence conservation with limited sequence divergence between genotypes, preferably of one or a few nucleotides, were identified as candidate targets for INVADER assays. Candidate probe oligonucleotides were designed by searching for stretches of sequence comprising a limited number of mismatches. Designs were generated to several sequences on either the sense or antisense strands. Suitable INVADER oligonucleotides were designed to accompany the respective probe oligonucleotide candidates. Several such probe and INVADER oligonucleotide pairs were designed to detect specific sequences associated with each of HCV genotypes 1-6. A probe set was also designed in a region of high sequence conservation across all sequences analyzed to serve as a positive internal control for the presence of the 5' UTR amplicon.

Candidate probe sets were then evaluated as described below on COBAS AMPLICOR viral load PCR amplicons generated from patient samples and characterized as to genotype by Inno-LiPA assays. Probe sets that generated signal of ≧5 FOZ and ≦ Approximately 25-30 FOZ were selected for further use on amplified DNA samples.

Screening Candidate Probe Sets

INVADER assays were performed in 96 well MJ Skirted microtiter plates. Plates were incubated using either an MJ Research PTC100 Thermocycler or a ThermoHybaid PCR Express (Molecular Biology Instrumentation, Needham Heights, Mass.) and read with an Applied Biosystems CYTOFLUOR® 4000 series multiwell plate reader.

INVADER assays to determine FOZ of probe sets were set up by preparing primary and secondary reaction master mixes as described above using either 7.5 μl of diluted template and 7.5 μl of INVADER master reaction mix or 10 μl of diluted template and 10 μl of INVADER master reaction mix. Oligonucleotides used in this experiments are presented in FIG. 3. Reactions were carried out in parallel in microtiter plates.

Master mixes were assembled as follows:
Volumes added
  4.67 μL FRET Buffer Mix (1.4 μM each FRET Cassette; 10.8% PEG; 43 mM MOPS pH 7.4)
  4.00 μL PI Mix (3.5 μM 1° Probe; 0.35 μM INVADER oligo)*
  1.33 μL CLEAVASE X enzyme/MgCl$_2$ (30 ng/μL CLEAVASE X enzyme; 210 mM MgCl$_2$)

10 μL Master Mix Concentrations

| FRET Cassette (each): | 0.65 μM |
| PEG (8000 MW): | 5% |
| MOPS (pH 7.4): | 20 mM |
| 1° Probe: | 1.4 μM* |
| INVADER oligo: | 0.14 μM* |
| CLEAVASE X enzyme: | 40 ng |
| MgCl$_2$: | 28 mM |

*Exceptions (final concentration in 10 μL Master Mix)
  Assay 8T: each probe is at 5× (7 μM)
  Assay 1C: INVADER oligo is at 10× (1.4 μM)
  Assay 2C: Probe is at 5× (7 μM)

Aliquots of 7.5 μl or 10 μl of each target at variable concentrations (PCR product diluted depending on the viral load, typically diluted 1:100 for COBAS AMPLICOR MONITOR or viral load samples and 1:500 for TAQMAN samples) were placed in the appropriate wells of a microtiter plate and were overlaid with 20 μl of mineral oil; 20 μl of 10 ng/μl tRNA were used for the no target control reactions. The targets were heat denatured at 98° C. for 10 minutes, cooled to 20° C., and then aliquots of 7.5 μl or 10 μl of the primary mix were added to each well (an amount of master mix equivalent in volume to the amount of target was added to each reaction). The microtiter plates were incubated for 60 minutes at 63° C.

The instrument gain was set for each dye so that the No Target Blank produced between 50-150 Relative Fluorescence Units (RFUs).

Because the optimal gain setting can vary between instruments, gain is adjusted as needed to ensure that the generated fluorescence signal is within the linear range of the specific instrument used. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

The raw data that is generated by the device/instrument is used to measure the assay performance (real-time or endpoint mode). The equations below provide how FOZ (Fold Over Zero), and other values are calculated. NTC in the equations below represents the signal from the No Target Control.

FOZ or Signal/No Target $$FOZ_{Dye1}=(RawSignal_{Dye1}/NTC_{Dye1})$$

Candidate probe sets for identifying each genotype were selected based on the relative signal generated in these experiments. In particular, desirable probe sets exhibit FOZs of ≧5 on appropriately diluted PCR product. FIG. 2 presents exemplary data obtained from testing six probe sets designed to detect genotype 3 on samples of known genotype. Similar experiments were carried out for candidate probe sets for the remaining genotypes 1,2,4-6. These results indicate that it is possible to discriminate HCV genotypes by using a select subset of polymorphisms within the 5' UTR. Probe sets that generated adequate genotype specific signal are presented in FIG. 3.

Example 2

Determination of Genotypes from AMPLICOR and TAQMAN Amplicons

Figure 4:
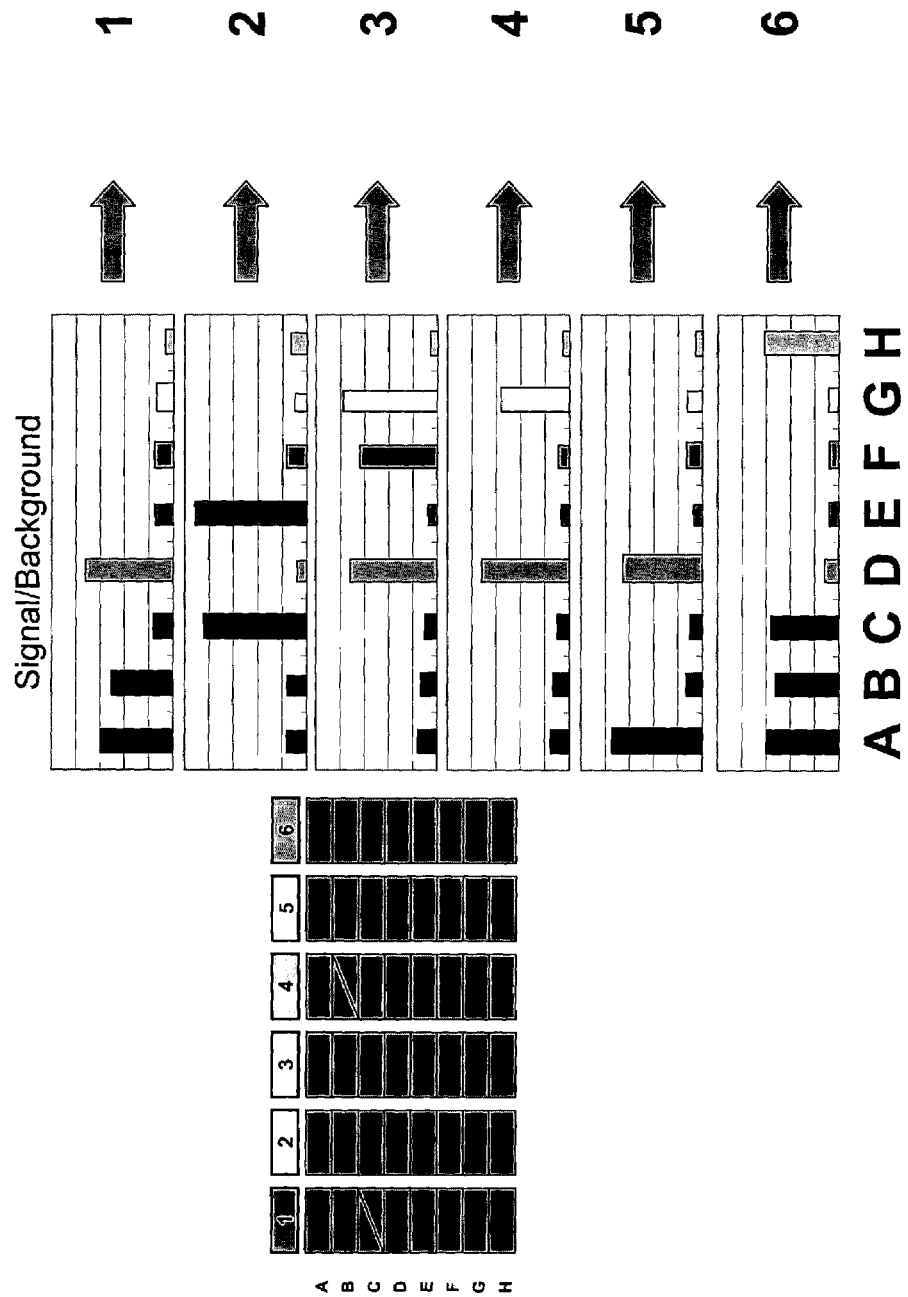
FIG. 4 shows a schematic of an HCV a 5' UTR genotype profile using the assay components of the present invention.

A total of eight separate INVADER reactions were identified as specific for between one and four different HCV genotypes. FIG. 4 presents a schematic illustration of how the HCV genotype matrix can be used to identify genotype based on results obtained from the eight selected probe sets. A ninth INVADER reaction was used as a positive control for the presence of DNA amplified from the 5' UTR.

Figure 5A:
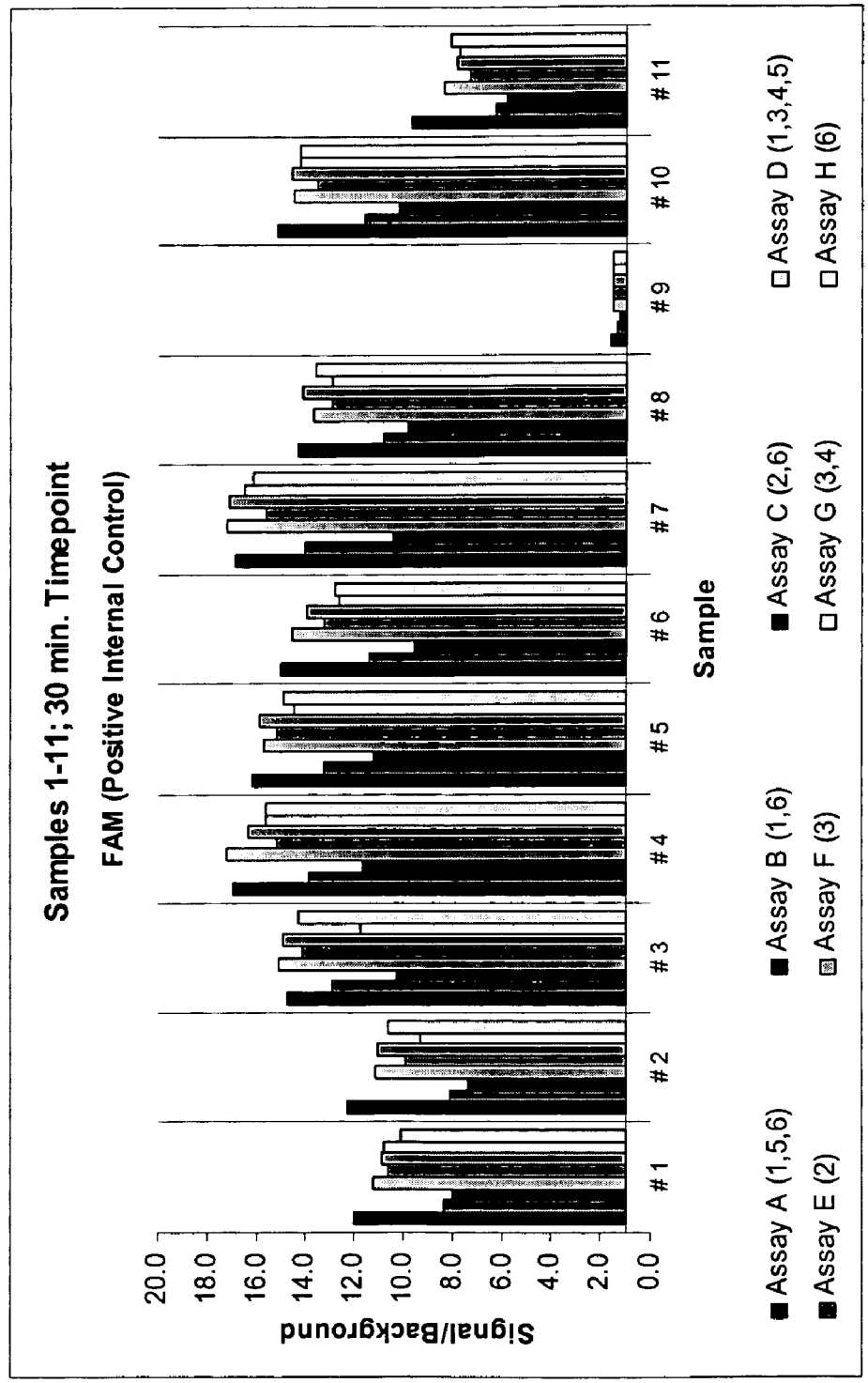
FIG. 5 shows the results of invasive cleavage assays carried out on PCR amplicons of the 5' UTR of HCV generated with COBAS AMPLICOR MONITOR reagents. A 5' UTR genotype profile for each of the eleven samples is shown in FIG. 5C.
Figure 5C:
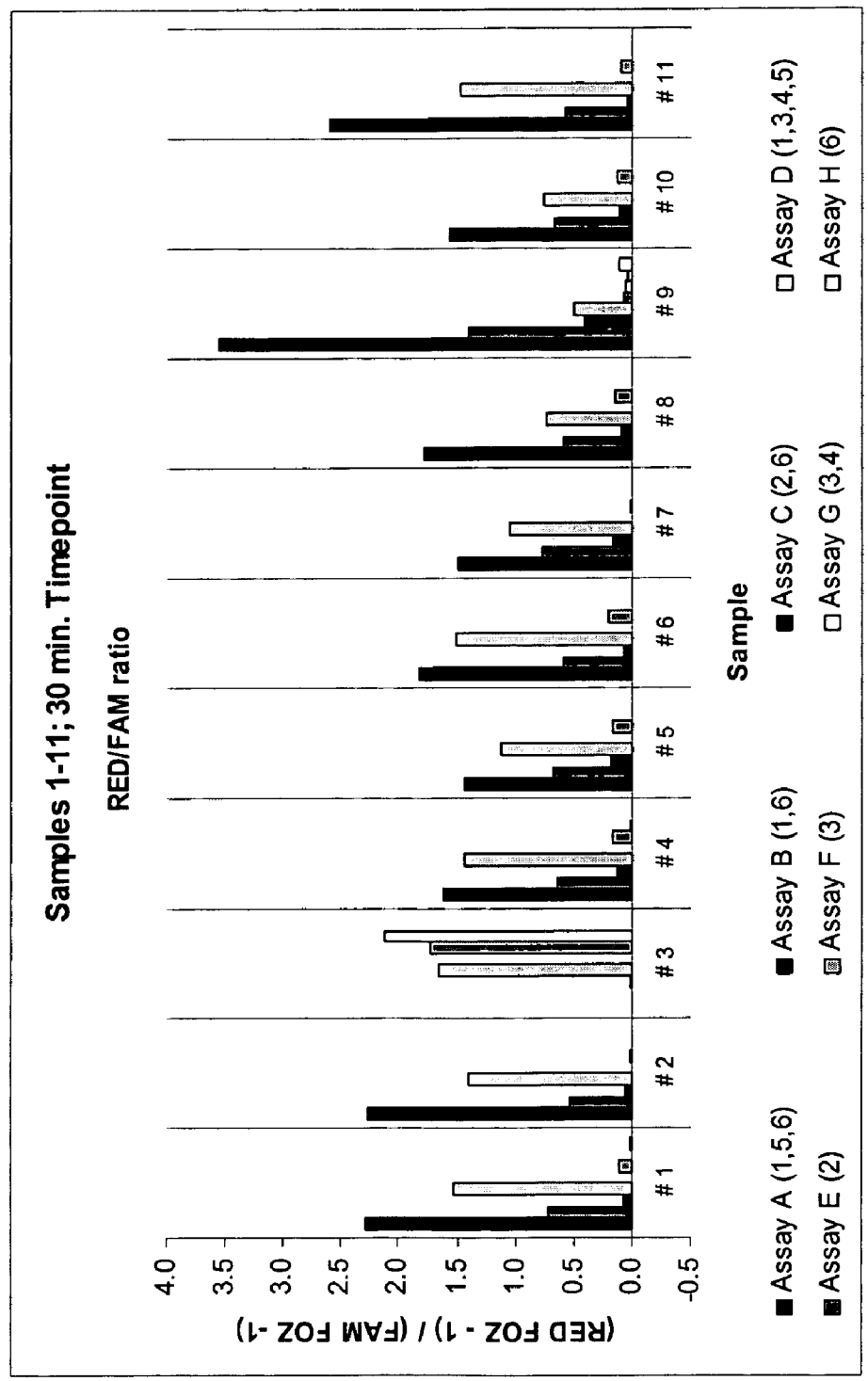
Figure 6A:
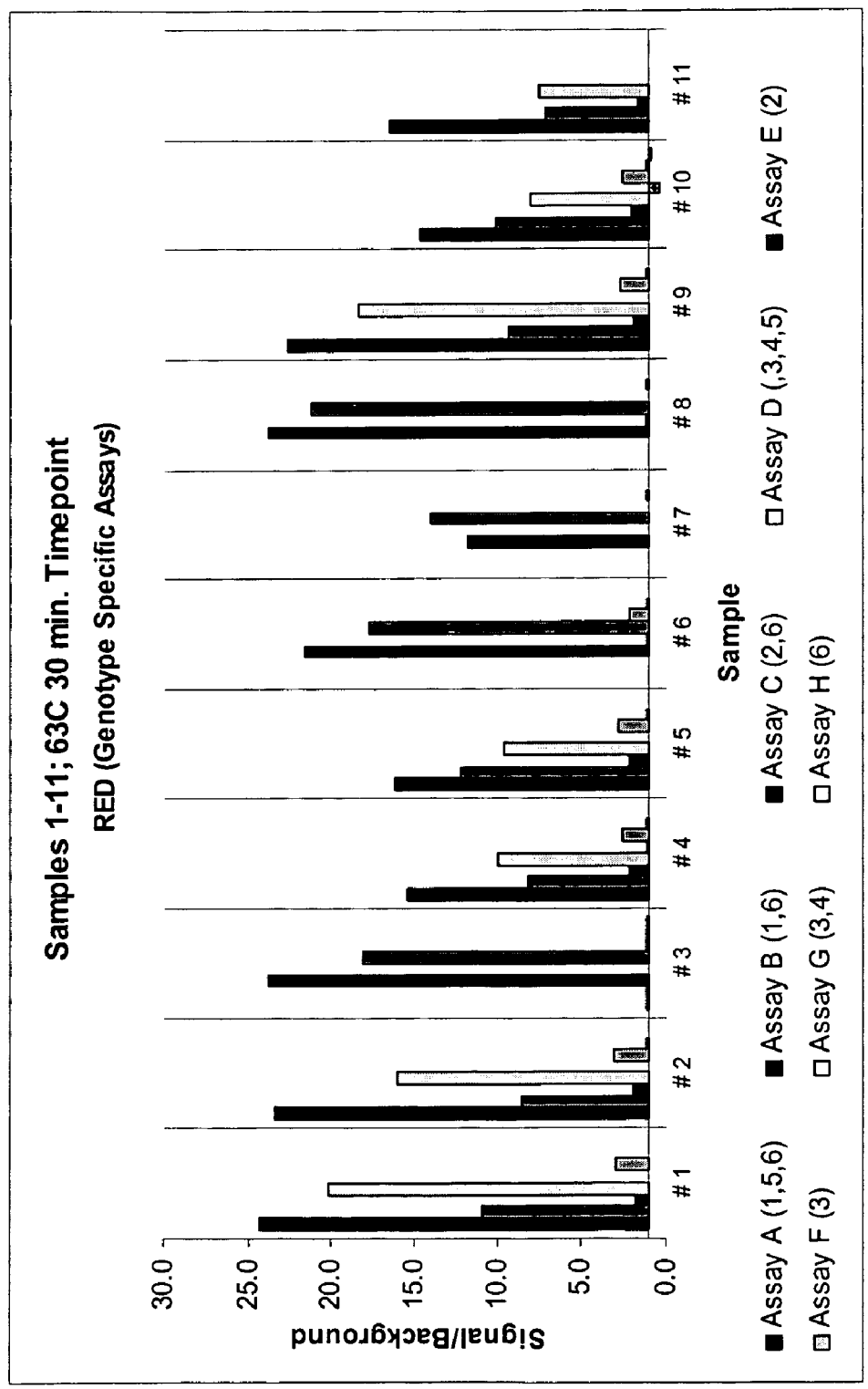
FIG. 6 shows the results of invasive cleavage assays carried out on PCR amplicons of the 5' UTR of HCV generated with COBAS TAQMAN reagents. A 5' UTR genotype profile for each of the eleven samples is shown in FIG. 6C.

Reactions were set up as described in Example 2, using 10 μl volumes of diluted target and INVADER reaction master mix. Reactions were incubated at 63° C. and read in a fluorescence microtiter plate reader as described above after 30 and 60 minutes. Exemplary data are presented in FIG. 5 for AMPLICOR MONITOR samples and FIG. 6 for TAQMAN samples. In each case, panel A presents FOZ data obtained from the internal control (FAM signal); panel B, from the genotype-specific probe sets (RED signal); and panel C, the ratios of the net FOZ (i.e. FOZ-1) of the RED and FAM signals. These data suggest that these eight probe sets can be used in combination to determine the genotype of HCV samples. A total of 115 samples were tested and yielded genotype results that were consistent with results obtained with other genotyping methods (i.e. Inno-LiPA reverse dot blot or TruGene sequencing). A total of three samples gave results that appeared to indicate the possibility of mixed infection or inadequate sample. Of the remaining samples, a total of four generated low signal across all probe sets tested. These samples were rediluted to varying extents in nuclease free water to determine their optimal dilution factor and retested. Upon retesting, these samples gave interpretable results concordant with results obtained via an alternative genotyping method.

Example 3

Co-Detection of Two HCV Genotypes in a Single Sample

In some cases, it is possible that a sample may contain more than one HCV genotype, e.g. due to co-infection by multiple strains. The ability of the INVADER assay to discern the presence of a mixed infection and to identify the genotypes present was tested.

Aliquots of AMPLICOR amplicons generated from samples of known genotype were mixed in the following ratios:

| Sample | Genotype 1 | Genotype 2 |
|--------|------------|------------|
| 1 | 50% | 50% |
| 2 | 75% | 25% |
| 3 | 90% | 10% |
| 4 | 95% | 5% |
| 5 | 25% | 75% |
| 6 | 10% | 90% |
| 7 | 5% | 95% |

Such mixtures were also made to combine amplicons from a genotype 1 and a genotype 3 sample, and a genotype 2 and a genotype 3 sample.

INVADER reactions were carried out on these artificially mixed samples as described in Example 2. Exemplary results are presented in FIG. 7 and suggest that in some cases it may be possible to discern infections in which two different genotypes are present at a 1:1 or 1:3 ratio or less.

Example 4

Design of Alternative Oligonucleotides to Detect Multiple HCV Strains

As in Example 1, the objective of these experiments was to arrive at oligonucleotide designs suitable for use in INVADER assays to detect particular sequences in the 5' UTR of HCV. Candidate sequences were identified as described in Example 1, and synthesized according to procedures standard in the art and purified by HPLC. Candidate probe sets were then evaluated as in Example 1 on COBAS AMPLICOR, AMPLICOR MONITOR, and TAQMAN viral load PCR amplicons generated from patient samples and characterized as to genotype by Inno-LiPA or TRUE-GENE HCV 5'NC genotyping kit assays. Probe sets that generated genotype-specific signal of ≧5 FOZ and ≦approximately 45-50 FOZ were selected for further use on amplified DNA samples.

Screening Candidate Probe Sets

INVADER assays were performed in 96 well MJ Skirted microtiter plates. Plates were incubated using either an MJ Research PTC100 Thermocycler or a ThermoHybaid PCR Express (Molecular Biology Instrumentation, Needham Heights, Mass.) and read with an Applied Biosystems CYTOFLUOR® 4000 series multiwell plate reader or a TECAN GENios FL pure microplate fluorometer.

INVADER assays to determine FOZ of probe sets were set up by preparing primary and secondary reaction master mixes as described above using either 7.5 µl of diluted template and 7.5 µl of INVADER master reaction mix or 10 µl of diluted template and 10 µl of INVADER master reaction mix. Oligonucleotides used in this experiments are presented in FIG. 8. Reactions were carried out in parallel in microtiter plates.

Master mixes were assembled as follows:
Volumes Added 5.00 µL FRET Buffer Mix (3.33 µM each FRET Cassette; 10 nM MOPS pH 7.4)

4.00 µL PI Mix (3.5 µL 1° Probe; 0.35 µL INVADER oligo)*

1.00 µL CLEAVASE X enzyme/MgCl$_2$ (30 ng/µL CLEAVASE X enzyme; 210 mM MgCl$_2$)

10 µL Master Mix Concentrations

| FRET Cassette (each): | 0.65 µM |
| PEG (8000 MW): | 5% |
| MOPS (pH 7.4): | 40 mM |
| 1° Probe: | 1.4 µM* |
| INVADER oligo: | 0.14 µM* |
| CLEAVASE X enzyme | 40 ng |
| MgCl$_2$: | 56 mM |

*Exceptions (Final Concentration in 10 µL Master Mix)

Assay 6G: Probe is at 5× (17.5 µM)

Assay 8T: Probe is at 0.5× (1.75 µM)

Assay 3T: INVADER oligo is at 10× (3.5 µM)

Assay 1C: Probes are at 0.5× (1.75 µM); INVADER oligo is at 10× (3.5 µM)

Assay 2C: Probe is at 5× (17.5 µM)

Aliquots of 7.5 µl or 10 µl of each sample amplicon at variable concentrations (PCR product diluted depending on the viral load, typically 1:20-1:500 dilution based on analytical methods and HCV viral load) were pipeted into appropriate wells of a microtiter plate and were overlaid with 20 µl of mineral oil; 20 µl of 10 ng/µl tRNA were used for the no target control reactions. The targets were heat denatured at 98° C. for 10 minutes, cooled to 63° C., and then aliquots of 7.5 µl or 10 µl of the INVADER HCV Genotyping Oligo master mix were added to each well (an amount of master mix equivalent in volume to the amount of target was added to each reaction). The microtiter plates were incubated for 60 minutes at 63° C. and read on an Applied Biosystems CYTOFLUOR® 4000 series multiwell plate reader at 30 minute and 60 minute intervals.

The instrument gain was set for each dye so that the No Target Blank produced between 50-150 Relative Fluorescence Units (RFUs). Data were analyzed as described in Example 1.

Figure 9:
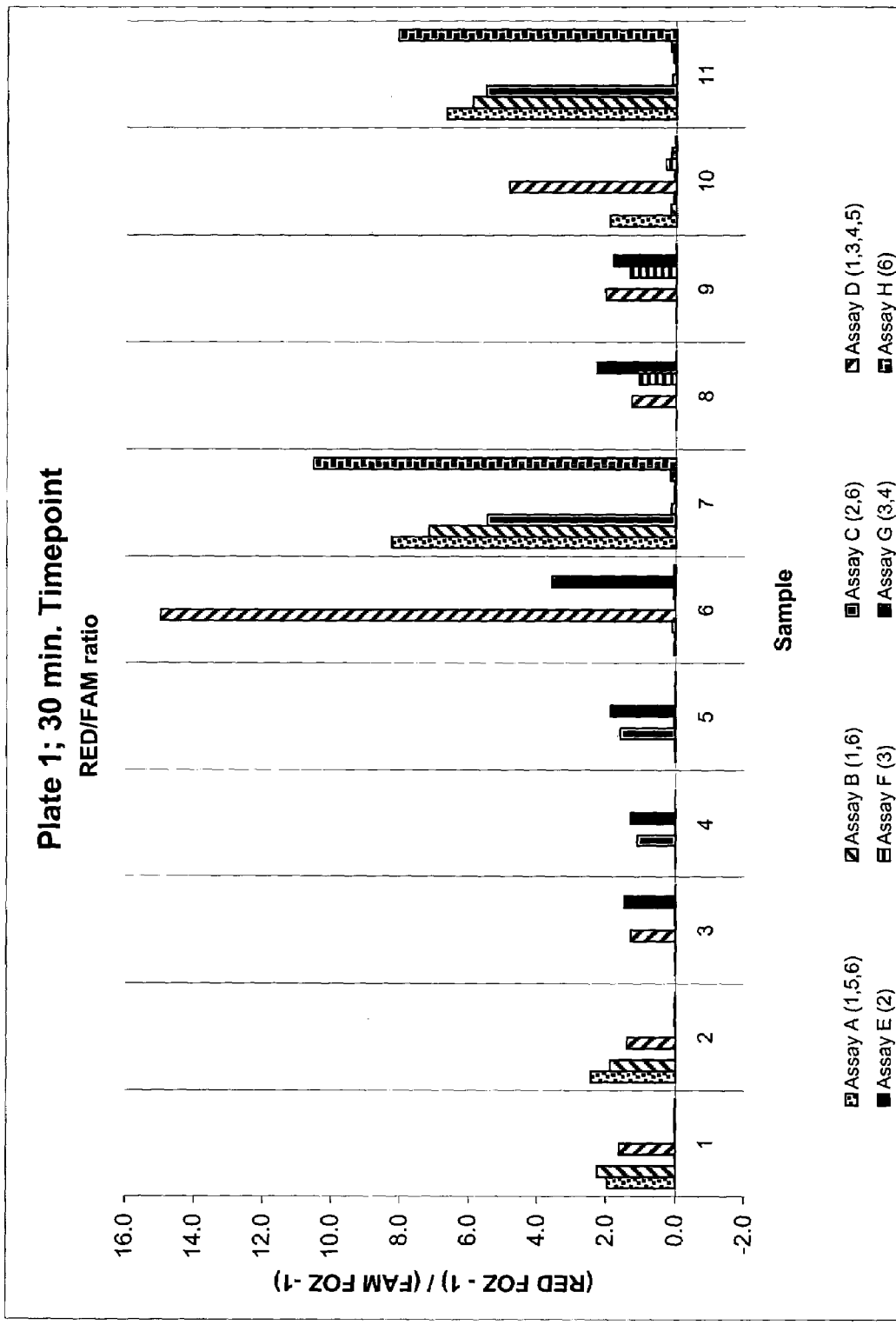
FIG. 9 shows the results of invasive cleavage assays carried out with alternative oligonucleotides on PCR amplicons of the 5' UTR of HCV. A 5' UTR genotype profile for each of the eleven samples is shown in this figure.

Exemplary results are presented in FIG. 9 and demonstrate the ability to discriminate between all six HCV genotypes from data obtained from the reaction of eight probe sets. Each probe set was selected based on the relative signal generated in these experiments described above. In particular, desirable probe sets exhibited genotype-specific FOZs of ≧5 and non-specific FOZs of ≦5 on appropriately diluted PCR product. In FIG. 9, the combination of eight probe sets in the "RED" and "FAM/RED ratio" graphs provided genotype determination obtained from the raw data results. It is noted that positive results for each assay are as follows: Assay A—detecting "G" at position −118; Assay B—detecting "A" at position −163; Assay C—detecting a "C" at position −80; Assay D—detecting a "T" at position −80; Assay E—detecting a "T" at position −155; Assay F—detecting a "C" at position −245; Assay G—detecting a "C" at position −167; and Assay H—detecting a "C" (CA insert) at position −144/5. As shown in the Figure legend in FIG. 9, and shown in the sequences in FIG. 10, these eight assays give a positive signal when the following genotypes are present in the sample: Assay A—positive for types 1, 5, and 6; Assay B—positive for types 1 and 6; Assay C—positive for types 2 and 6; Assay D—positive for types 1, 3, 4, and 5; Assay E—positive for type 2; Assay F—positive for type 3; Assay G—positive for types 3 and 4; and Assay H—positive for type 6.

The results generated for each sample reveal a 5' UTR genotype profile compiled for each sample (see FIG. 9) which in turn allows the HCV genotype present in each sample to be determined based on only examining SNPs in the 5' UTR of HCV. For example, sample 1 (shown in FIG. 9) was determined to be Genotype I in light of the positive result from Assay A (positive for genotypes 1, 5, and 6), Assay B (positive for genotypes 1 and 6) and Assay D (positive for genotypes 1, 3, 4, and 5) since the only genotype number these three all have in common is Genotype I. The negative results in Assay C (positive for genotypes 2 and 6), Assay E (positive for genotype 2), Assay F (positive for genotype 3), Assay G (positive for genotype 3 and 4) and Assay H (positive for genotype 6) confirms the determination that this sample contains Genotype I. In other words, the combined results of this plurality of assays (e.g. through the process of elimination) allows a determination that this sample contains Genotype I. This determination can be simplified by looking at the genotype matrix provided in FIG. 4, as well as the base specific genotype matrix in Table 1 below (as well as looking at the base positions in each Genotype at detected positions in FIG. 10). This same procedure can be employed for the remaining 10 samples shown in FIG. 9, to generate the following results: sample 2 contains Genotype 1; sample 3 contains Genotype 4; sample 4 contains Genotype 2; sample 5 contains Genotype 2; sample 6 contains Genotype 4; sample 7 contains Genotype 6; sample 8 contains Genotype 3; sample 9 contains Genotype 3; sample 10 contains Genotype 5; and sample 11 contains Genotype 6. Of course other combinations of assay (other than all 8 assays) can be used to generate a 5' UTR genotype profile which in turn can be used to assign a genotype to a detected HCV. Thus, a select subset of polymorphisms within the 5' UTR enables probe sets to generate adequate genotype-specific signal as presented in FIG. 9.

TABLE 1

| Site | Assay | Genotype | | | | | |
|---|---|---|---|---|---|---|---|
| | | 1 | 2 | 3 | 4 | 5 | 6 |
| (−245) | F | T | T | C | T | T | T |
| (−167) | G | T | T | C | C | T | T |
| (−163) | B | A | G | G | G | G | A |
| (−155) | E | C | T | C | C | C | C |
| (−144/5) | H | / | / | / | / | / | CA |
| (−118) | A | G | C | A | A | G | G |
| (−80) | C + D | T | C | T | T | T | C |

Example 5

Identification of Genotype-Specific SNP Sets

In some cases, it is possible to identify a limited subset of single nucleotide polymorphisms (SNPs) within the 5' UTR that can be used to identify genotype. Based on an alignment of approximately 200 sequences obtained from public databases, the following SNPs or sets of SNPs in Table 2 were identified as sufficient to identify the indicated genotypes.

TABLE 2

| Type 1 | A −163 AND no CA −144/5 and no C −167 (or and T −167) |
|---|---|
| | A −163 AND T −80 and no C −167 (T −167) |
| | A −163 AND C −72 and no C −167 (T −167) |
| | T −122 AND no CA −144/5 and no C −167 |
| | T −122 AND T −80 and no C −167 |
| | T −122 AND C −72 and no C −167 |
| Type 2 | −155 T |
| | −132 A and G −163 |
| | −128 T |
| | −119 Y and no C −167 (T −167) |
| | −117 C |
| Type 3 | −245 C |
| Type 4 | −245T AND −167C |
| | −245 T AND −118A |
| Type 5 | −167T AND −163G AND −155C |
| | −122C AND −117G |
| Type 6 | CA −144/5 |
| | −117G AND −80C |
| | −118 A AND −80 C |
| | −122 T AND −80 C |
| | −122 T AND −72T |

All publications and patents mentioned in the above specification are herein incorporated by reference as if expressly set forth herein. Various modifications and variations of the described assays of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

SEQUENCE LISTING

<160> NUMBER OF SEQ ID NOS: 69

<210> SEQ ID NO 1
<211> LENGTH: 42
<212> TYPE: DNA
<213> ORGANISM: Artificial Sequence
<220> FEATURE:
<223> OTHER INFORMATION: Synthetic

<400> SEQUENCE: 1
gctgcacgaa ggctagcggt ctcgcagggg cgcgcctaaa ta                                42

<210> SEQ ID NO 2
<211> LENGTH: 32
<212> TYPE: DNA
<213> ORGANISM: Artificial Sequence
<220> FEATURE:
<223> OTHER INFORMATION: Synthetic

<400> SEQUENCE: 2
acggacgcgg agctccagac attgggcggg tt                                          32

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
acggacgcgg agctccagac attgggcggg                                             30

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
acggacgcgg agctccgggc atcgagc                                                27

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
cagccgcggg ttcatccgag aaagggcccg gccgtcca                                    38

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
tggccgagga tccaatggaa agggcccggt catcca                                      36

<210> SEQ ID NO 7
<211> LENGTH: 34

```
<212> TYPE: DNA
<213> ORGANISM: Artificial Sequence
<220> FEATURE:
<223> OTHER INFORMATION: Synthetic

<400> SEQUENCE: 7
acggacgcgg agtggcaatc ccggtgcact cacc                          34

<210> SEQ ID NO 8
<211> LENGTH: 28
<212> TYPE: DNA
<213> ORGANISM: Artificial Sequence
<220> FEATURE:
<223> OTHER INFORMATION: Synthetic

<400> SEQUENCE: 8
acggacgcgg agtgccaatt gcggtgta                                 28

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9
cctgccgtgc ctccgcagga ctgccagccg ggtaga                        36

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
acggacgcgg agcgttgggt tgcgaa                                   26

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
cctgccgtgc ctccgcgaga ccgctggccg ggtaga                        36

<210> SEQ ID NO 12
<211> LENGTH: 37
<212> TYPE: DNA
<213> ORGANISM: Artificial Sequence
<220> FEATURE:
<223> OTHER INFORMATION: Synthetic

<400> SEQUENCE: 12
gcggtgggtg cctccgcgag atcactagcc gggtaga                       37

<210> SEQ ID NO 13
<211> LENGTH: 37
<212> TYPE: DNA
<213> ORGANISM: Artificial Sequence
<220> FEATURE:
<223> OTHER INFORMATION: Synthetic

<400> SEQUENCE: 13
```

-continued

```
cgggcgcgtg cctccgcagg actgccagcc gggtaga                                    37

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
acggacgcgg agtgttgggc cgcgaaa                                               27

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
ccggccgggc atagagtggg ttaatccgag aaaagaccct                                 40

<210> SEQ ID NO 16
<211> LENGTH: 31
<212> TYPE: DNA
<213> ORGANISM: Artificial Sequence
<220> FEATURE:
<223> OTHER INFORMATION: Synthetic

<400> SEQUENCE: 16
acggacgcgg agagtctttc cggtaattcc g                                          31

<210> SEQ ID NO 17
<211> LENGTH: 31
<212> TYPE: DNA
<213> ORGANISM: Artificial Sequence
<220> FEATURE:
<223> OTHER INFORMATION: Synthetic

<400> SEQUENCE: 17
acggacgcgg agagtcttcc cggcagttcc g                                          31

<210> SEQ ID NO 18
<211> LENGTH: 36
<212> TYPE: DNA
<213> ORGANISM: Artificial Sequence
<220> FEATURE:
<223> OTHER INFORMATION: Synthetic

<400> SEQUENCE: 18
ccgctcgcgg aaagcgccta gccgtggcgt tggtaa                                     36

<210> SEQ ID NO 19
<211> LENGTH: 31
<212> TYPE: DNA
<213> ORGANISM: Artificial Sequence
<220> FEATURE:
<223> OTHER INFORMATION: Synthetic

<400> SEQUENCE: 19
acggacgcgg agcgagtggc gtgcggcctc c                                          31

<210> SEQ ID NO 20
<211> LENGTH: 37
<212> TYPE: DNA
<213> ORGANISM: Artificial Sequence
```

```
<220> FEATURE:
<223> OTHER INFORMATION: Synthetic

<400> SEQUENCE: 20
caggtcccgt ccaaggaagg atccggtcat cccggct                              37

<210> SEQ ID NO 21
<211> LENGTH: 37
<212> TYPE: DNA
<213> ORGANISM: Artificial Sequence
<220> FEATURE:
<223> OTHER INFORMATION: Synthetic

<400> SEQUENCE: 21
caggtcccgt ccaaggaagg atccggtcac cccagct                              37

<210> SEQ ID NO 22
<211> LENGTH: 32
<212> TYPE: DNA
<213> ORGANISM: Artificial Sequence
<220> FEATURE:
<223> OTHER INFORMATION: Synthetic

<400> SEQUENCE: 22
acggacgcgg aggattacgg tgtagtcacc gg                                   32

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
ggacacggac tccagggatt gagtgggttt ggtccaatc                            39

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
acggacgcgg agggaaaggg cccggtc                                         27

<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25
cacccggagg accctgtcgt cccggcgatt ccggcgtact cgccggta                  48

<210> SEQ ID NO 26
<211> LENGTH: 30
<212> TYPE: DNA
<213> ORGANISM: Artificial Sequence
<220> FEATURE:
<223> OTHER INFORMATION: Synthetic

<400> SEQUENCE: 26
acggacgcgg agtccgcagg ccactacggc                                      30
```

<210> SEQ ID NO 27
<211> LENGTH: 32
<212> TYPE: DNA
<213> ORGANISM: Artificial Sequence
<220> FEATURE:
<223> OTHER INFORMATION: Synthetic

<400> SEQUENCE: 27
agccggtttt ccggctgaga ctccgcgtcc gt					32

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
agccggtttt ccggctgaga cctcggcgcg					30

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
gctgcacgaa ggctagcggt ctcgcagggg cgcgcctaaa ta					42

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
acggacgcgg agctccagac attgggcggg tt					32

<210> SEQ ID NO 31
<211> LENGTH: 50
<212> TYPE: DNA
<213> ORGANISM: Artificial Sequence
<220> FEATURE:
<223> OTHER INFORMATION: Synthetic

<400> SEQUENCE: 31
cgacctaccg gcattgggcg ggttcatccg agaaagggcc cggccgtcca					50

<210> SEQ ID NO 32
<211> LENGTH: 38
<212> TYPE: DNA
<213> ORGANISM: Artificial Sequence
<220> FEATURE:
<223> OTHER INFORMATION: Synthetic

<400> SEQUENCE: 32
cagccgcggg ttcatccgag aaagggcccg gccgtcca					38

<210> SEQ ID NO 33
<211> LENGTH: 40
<212> TYPE: DNA
<213> ORGANISM: Artificial Sequence
<220> FEATURE:
<223> OTHER INFORMATION: Synthetic

```
<400> SEQUENCE: 33
acggacgcgg agtggcaatc ccggtgcact cactggttcc                                40

<210> SEQ ID NO 34
<211> LENGTH: 28
<212> TYPE: DNA
<213> ORGANISM: Artificial Sequence
<220> FEATURE:
<223> OTHER INFORMATION: Synthetic

<400> SEQUENCE: 34
acggacgcgg agtgccaatt gcggtgta                                             28

<210> SEQ ID NO 35
<211> LENGTH: 36
<212> TYPE: DNA
<213> ORGANISM: Artificial Sequence
<220> FEATURE:
<223> OTHER INFORMATION: Synthetic

<400> SEQUENCE: 35
cctgccgtgc ctccgcagga ctgccagccg ggtaga                                    36

<210> SEQ ID NO 36
<211> LENGTH: 36
<212> TYPE: DNA
<213> ORGANISM: Artificial Sequence
<220> FEATURE:
<223> OTHER INFORMATION: Synthetic

<400> SEQUENCE: 36
tccgcgcgtc ccgttgagtt gcggaaggtc ttgtgg                                    36

<210> SEQ ID NO 37
<211> LENGTH: 37
<212> TYPE: DNA
<213> ORGANISM: Artificial Sequence
<220> FEATURE:
<223> OTHER INFORMATION: Synthetic

<400> SEQUENCE: 37
gcggtgggtg ccctgcgag attgctagct gagtaga                                    37

<210> SEQ ID NO 38
<211> LENGTH: 37
<212> TYPE: DNA
<213> ORGANISM: Artificial Sequence
<220> FEATURE:
<223> OTHER INFORMATION: Synthetic

<400> SEQUENCE: 38
gcggtgggtg cctccgctag accactagct gagtaga                                   37

<210> SEQ ID NO 39
<211> LENGTH: 37
<212> TYPE: DNA
<213> ORGANISM: Artificial Sequence
<220> FEATURE:
<223> OTHER INFORMATION: Synthetic

<400> SEQUENCE: 39
gcggtgggtg cctccgctag accgctagct gagtaga                                   37

<210> SEQ ID NO 40
```

<211> LENGTH: 37
<212> TYPE: DNA
<213> ORGANISM: Artificial Sequence
<220> FEATURE:
<223> OTHER INFORMATION: Synthetic

<400> SEQUENCE: 40
gcggtgggtg cccctgcgag attgctagct gagtgga     37

<210> SEQ ID NO 41
<211> LENGTH: 36
<212> TYPE: DNA
<213> ORGANISM: Artificial Sequence
<220> FEATURE:
<223> OTHER INFORMATION: Synthetic

<400> SEQUENCE: 41
cctgccgtgc ctccgcagga ctgccagccg ggtaga     36

<210> SEQ ID NO 42
<211> LENGTH: 37
<212> TYPE: DNA
<213> ORGANISM: Artificial Sequence
<220> FEATURE:
<223> OTHER INFORMATION: Synthetic

<400> SEQUENCE: 42
acggacgcgg agtgttgagt cgcggaaggt cttgtgg     37

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
acggacgcgg agtattgggc cgcgaaa     27

<210> SEQ ID NO 44
<211> LENGTH: 52
<212> TYPE: DNA
<213> ORGANISM: Artificial Sequence
<220> FEATURE:
<223> OTHER INFORMATION: Synthetic

<400> SEQUENCE: 44
cgcgccccca aagtggccgg acatagggtg ggttcatccg agaagggacc ct     52

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
acggacgcgg agagtctttc cggtaattcc g     31

<210> SEQ ID NO 46
<211> LENGTH: 33
<212> TYPE: DNA
<213> ORGANISM: Artificial Sequence
<220> FEATURE:
<223> OTHER INFORMATION: Synthetic

<400> SEQUENCE: 46
acggacgcgg agagtctttc cggcagttcc ggt          33

<210> SEQ ID NO 47
<211> LENGTH: 33
<212> TYPE: DNA
<213> ORGANISM: Artificial Sequence
<220> FEATURE:
<223> OTHER INFORMATION: Synthetic

<400> SEQUENCE: 47
acggacgcgg agagtcttct cggcagttcc ggt          33

<210> SEQ ID NO 48
<211> LENGTH: 36
<212> TYPE: DNA
<213> ORGANISM: Artificial Sequence
<220> FEATURE:
<223> OTHER INFORMATION: Synthetic

<400> SEQUENCE: 48
ccgctcgcgg aaagcgccta gccgtggcgt tggtaa       36

<210> SEQ ID NO 49
<211> LENGTH: 29
<212> TYPE: DNA
<213> ORGANISM: Artificial Sequence
<220> FEATURE:
<223> OTHER INFORMATION: Synthetic

<400> SEQUENCE: 49
acggacgcgg agcgagtggc gaacggcct               29

<210> SEQ ID NO 50
<211> LENGTH: 29
<212> TYPE: DNA
<213> ORGANISM: Artificial Sequence
<220> FEATURE:
<223> OTHER INFORMATION: Synthetic

<400> SEQUENCE: 50
acggacgcgg agcgagtggc gtgcggcct               29

<210> SEQ ID NO 51
<211> LENGTH: 42
<212> TYPE: DNA
<213> ORGANISM: Artificial Sequence
<220> FEATURE:
<223> OTHER INFORMATION: Synthetic

<400> SEQUENCE: 51
ggcgtccggg ttgctccagg aaagggcccg gtccccccgg ct    42

<210> SEQ ID NO 52
<211> LENGTH: 42
<212> TYPE: DNA
<213> ORGANISM: Artificial Sequence
<220> FEATURE:
<223> OTHER INFORMATION: Synthetic

<400> SEQUENCE: 52
ggcgtccggg ttgctccagg aaagggcccg gtcccccag ct    42

<210> SEQ ID NO 53
<211> LENGTH: 42
<212> TYPE: DNA

```
<213> ORGANISM: Artificial Sequence
<220> FEATURE:
<223> OTHER INFORMATION: Synthetic

<400> SEQUENCE: 53
ggcgtccggg ttgctccagg aaagggcccg gtcctcctgg ct                          42

<210> SEQ ID NO 54
<211> LENGTH: 42
<212> TYPE: DNA
<213> ORGANISM: Artificial Sequence
<220> FEATURE:
<223> OTHER INFORMATION: Synthetic

<400> SEQUENCE: 54
ggcgtccggg ttgctccagg aaagggcccg gtcctcccgg ct                          42

<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
acggacgcgg aggattacgg tggactcacc                                        30

<210> SEQ ID NO 56
<211> LENGTH: 38
<212> TYPE: DNA
<213> ORGANISM: Artificial Sequence
<220> FEATURE:
<223> OTHER INFORMATION: Synthetic

<400> SEQUENCE: 56
ggcggcatcc ccaggcagtg agagggtttg gtccaatc                               38

<210> SEQ ID NO 57
<211> LENGTH: 27
<212> TYPE: DNA
<213> ORGANISM: Artificial Sequence
<220> FEATURE:
<223> OTHER INFORMATION: Synthetic

<400> SEQUENCE: 57
acggacgcgg agggaaaggg cccggtc                                           27

<210> SEQ ID NO 58
<211> LENGTH: 41
<212> TYPE: DNA
<213> ORGANISM: Artificial Sequence
<220> FEATURE:
<223> OTHER INFORMATION: Synthetic

<400> SEQUENCE: 58
aaccgggccg gtgtgctcgc cggttcggca gaccgctatg c                           41

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
cgcgccgagg gctctctcgg gagg                                              24
```

<210> SEQ ID NO 60
<211> LENGTH: 32
<212> TYPE: DNA
<213> ORGANISM: Artificial Sequence
<220> FEATURE:
<223> OTHER INFORMATION: Synthetic

<400> SEQUENCE: 60
agccggtttt ccggctgaga ctccgcgtcc gt         32

<210> SEQ ID NO 61
<211> LENGTH: 30
<212> TYPE: DNA
<213> ORGANISM: Artificial Sequence
<220> FEATURE:
<223> OTHER INFORMATION: Synthetic

<400> SEQUENCE: 61
agccggtttt ccggctgaga cctcggcgcg         30

<210> SEQ ID NO 62
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: This residue is linked to a Z28 quenching
      group.

<400> SEQUENCE: 62
tcttcggcct tttggccgag agaggacgcg cgga         34

<210> SEQ ID NO 63
<211> LENGTH: 35
<212> TYPE: DNA
<213> ORGANISM: Artificial Sequence
<220> FEATURE:
<223> OTHER INFORMATION: Synthetic

<400> SEQUENCE: 63
tccgcgcgtc ccgttgagtt gcggacggtc ttgtg         35

<210> SEQ ID NO 64
<211> LENGTH: 244
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t

<400> SEQUENCE: 64
gcaraaagcg yytagccatg gcgttagtat gagtgtygtr yarcytccag gnyccccyt         60 cccgggagag ccatrgtggt ctscggaacc ggtgagwaca ccgyaattgc caggabgacc       120
gggtcctttc ttggathamc ccgctcaatg cctggagatt tgggcgtgcc cccgcragac       180
ygctagccga gtagtgttgg gtcgcgaaag gccttgtggt actgcctgat agggtgcttg       240
cgag                                                                    244

<210> SEQ ID NO 65
<211> LENGTH: 244
<212> TYPE: DNA
<213> ORGANISM: Artificial Sequence
<220> FEATURE:
<223> OTHER INFORMATION: Synthetic

<400> SEQUENCE: 65

```
gcagaaagcg yctarccatg gcgttagtat gagtgtcgta cagcctccag gccccccct      60
cccgggagag ccatagtggt ctgcggaacc ggtgagtaca ccggaattrc cggraagact    120
gggtcctttc ttggryaaac ccactctrtg yccggycrtt tgggcrygcc cccgcaagac    180
ygctagccka gtagcgttgg gttgcgaamg gccttgtggt actgcctgat agggygcttg    240
cgag                                                                 244
```

<210> SEQ ID NO 66
<211> LENGTH: 244
<212> TYPE: DNA
<213> ORGANISM: Artificial Sequence
<220> FEATURE:
<223> OTHER INFORMATION: Synthetic

<400> SEQUENCE: 66

```
gcggaaagcg yctagccatg gcgttagtac gagtgtcgtg cagcctccag gmcccccct     60
yccgggagag ccatagtggt ctgcggaacc ggtgagtaca ccggaatcgc ygggdtgacc   120
gggtcctttc ttggarcwac ccgctcaatr cccrgaaatt tgggcgtgcc cccgcragay   180
yrctagccga gtagtgttgg gtcgcgaaag gccttgtggt actgcctgat agggygcttg   240
cgag                                                                244
```

<210> SEQ ID NO 67
<211> LENGTH: 244
<212> TYPE: DNA
<213> ORGANISM: Artificial Sequence
<220> FEATURE:
<223> OTHER INFORMATION: Synthetic

<400> SEQUENCE: 67

```
gcagaaagcg tctagccatg gcgttagtat gagtgttgta cagcctccag gacccccct    60
cccgggagag ccatagtggt ctkcggaacc ggtgagtaca ccggaatcgc cgggatgacc  120
gggtcctttc ttggattaac ccgctcaatg cccgaaatt tgggcgtgcc cccgcaagac   180
tgctagccga gtagtgttgg gtcgcgaaag gccttgyggt actgcctgat agggtgcttg  240
cgag                                                               244
```

<210> SEQ ID NO 68
<211> LENGTH: 244
<212> TYPE: DNA
<213> ORGANISM: Artificial Sequence
<220> FEATURE:
<223> OTHER INFORMATION: Synthetic

<400> SEQUENCE: 68

```
gcagaaagcg tctagccatg gcgttagtat gagtgtcgaa cagcctccag gacccccct    60
cccgggagag ccatagtggt ctgcggaacc ggtgagtaca ccggaattgc cgggatgacc  120
gggtcctttc ttggataaac ccgctcaatg cccggagatt tgggcgtgcc cccgcgagac  180
tgctagccga gtagtgttgg gtcgcgaaag gccttgtggt actgcctgat agggtgcttg  240
cgag                                                               244
```

-continued

```
<210> SEQ ID NO 69
<211> LENGTH: 247
<212> TYPE: DNA
<213> ORGANISM: Artificial Sequence
<220> FEATURE:
<223> OTHER INFORMATION: Synthetic

<400> SEQUENCE: 69
gcagaaagcg tctagccatg gcgttagtat gagtgtcgtr cagcctccag gccccccct        60 cccgsgagag ccatagtrgt ctgcggaacc ggtgagtaca ccggaattgc caggaygacc      120
gggtcctttc cattggatca aacccgctca atgcctggag atttgggcgt gccccgcaa      180 gactgctagc cgagtagcgt tgggttgcga aaggccttgt ggtactgcct gatagggtgc      240
ttgcgag                                                                247
```

Figure 10:
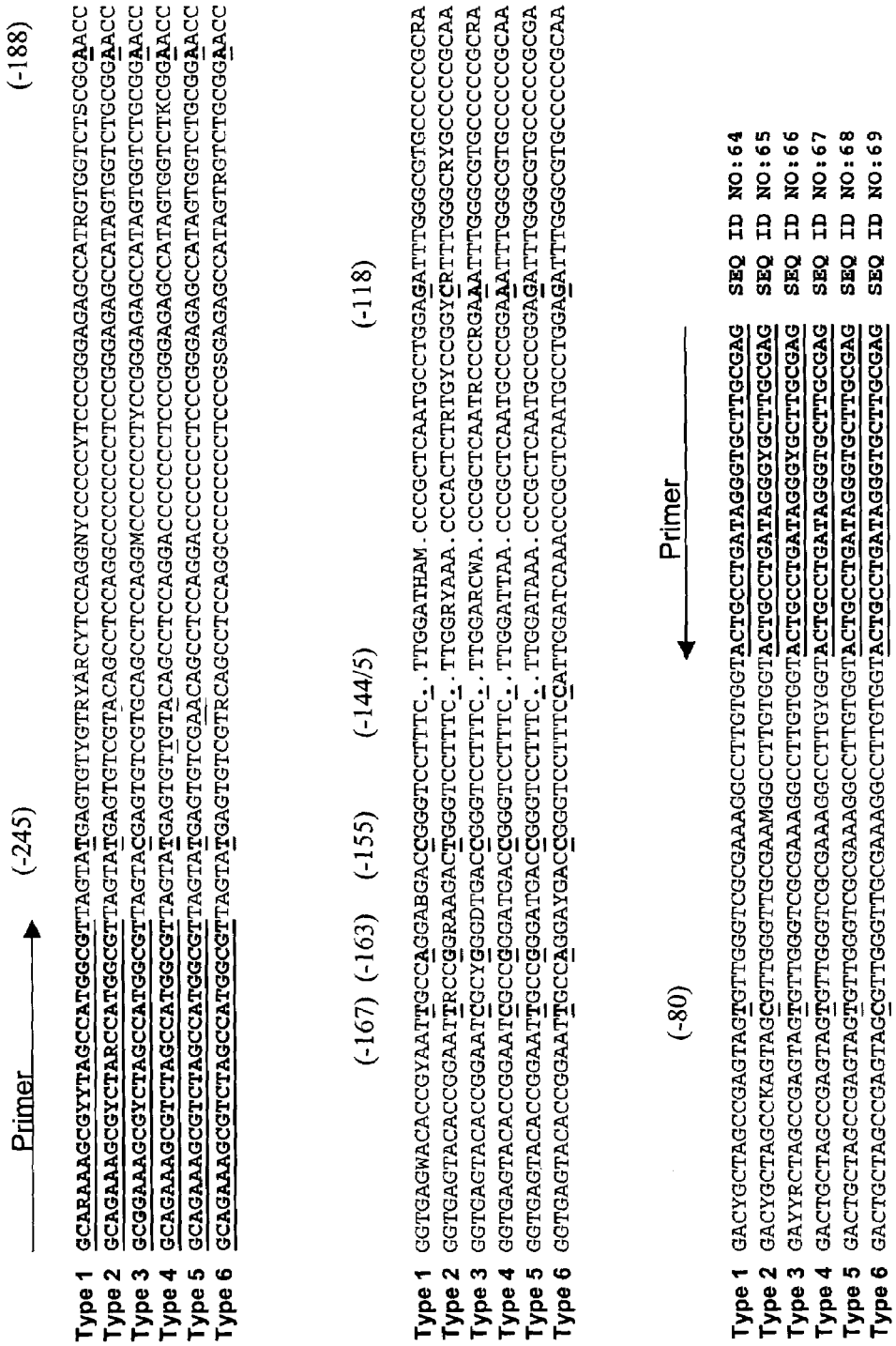
FIG. 10 shows an alignment of the consensus sequence for each of the six HCV genotypes in a region of the 5' UTR of HCV from −274 to −31. The sequence from each of the six genotypes is labeled as follows: Genotype I (SEQ ID NO:64); Genotype II (SEQ ID NO:65); Genotype III (SEQ ID NO:66); Genotype IV (SEQ ID NO:67); Genotype V (SEQ ID NO:68); and Genotype VI (SEQ ID NO:69). Also, various single nucleotide polymorphism positions are labeled including −245; −188 (control); −167; −163; −155; −144/5; −118; and −80; which are detected in certain embodiments of the present invention to provide at least partial genotype information (which can be determined by referring to this figure). This figure also shows the position of exemplary primers that may be used to amplify this region of the 5' UTR of HCV.

We claim:

1. A method for determining the genotype of hepatitis C virus in a sample comprising;
   a) providing;
      i) a sample from a subject, wherein said sample is suspected of containing hepatitis C virus, and
      ii) two or more probe sets, wherein each of probe sets is configured for detecting a single nucleotide polymorphism in a 5' UTR sequence of HCV, and
   b) contacting said sample with said two or more probe sets under conditions such that at least partial genotype information for each of said single nucleotide polymorphisms is determined thereby generating a 5' UTR genotype profile, wherein said 5' UTR genotype profile comprises at least partial genotype information for single nucleotide polymorphisms located in at least two of the following positions: −245, −167, −163, −155, −144/5, −118, and −80; wherein said positions are found in SEQ ID NOs 64, 65, 66, 67, 68 and 69 as shown in FIG. 10, and wherein said 5' UTR genotype profile is sufficient to genotype said hepatitis C virus.

2. The method of claim 1, further comprising c) genotyping said hepatitis C virus based on said 5' UTR genotype profile as Genotype I, II, IV, V, or VI.

3. The method of claim 2, wherein said genotyping classifies said hepatitis C virus as being Genotype I, IV or V.

4. The method of claim 1, wherein said two or more probe sets comprise invasive cleavage structure type probes.

5. The method of claim 1, wherein each probe set comprises a first oligonucleotide, wherein said first oligonucleotide comprises a 5' portion and a 3' portion, wherein said 3' portion is configured to hybridize to said 5' UTR sequence of HCV, and wherein said 5' portion is configured to not hybridize to said 5' UTR sequence of HCV.

6. The method of claim 1, wherein each probe set comprises a second oligonucleotide, wherein said second oligonucleotide comprises a 5' portion and a 3' portion, wherein said 5' portion is configured to hybridize to said 5' UTR sequence of HCV, and wherein said 3' portion is configured to not hybridize to said 5' UTR sequence of HCV.

7. The method of claim 1, wherein said 5' UTR genotype profile comprises: i) an A at position −163, and ii) no C at position −144, and wherein the method further comprises genotyping said hepatitis C virus based on said 5' UTR genotype profile as Genotype I.

8. The method of claim 7, wherein said 5' UTR genotype profile further comprises: iii) no C at position −167, or a T at position −167.

9. The method of claim 1, wherein said 5' UTR genotype profile comprises: i) an A at position −163, and ii) a T at position −80, wherein the method further comprises genotyping said hepatitis C virus based on said 5' UTR genotype profile as Genotype I.

10. The method of claim 9, wherein said 5' UTR genotype profile further comprises: iii) no C at position −167, or a T a position −167.

11. The method of claim 1, wherein said 5' UTR genotype profile comprises: i) an A at position −163, and ii) a C at position −72, and wherein the method further comprises genotyping said hepatitis C virus based on said 5' UTR genotype profile as Genotype I.

12. The method of claim 11, wherein said 5' UTR genotype profile further comprises: iii) no C at position −167, or a T a position −167.

13. The method of claim 1, wherein said 5' UTR genotype profile comprises: i) a T at position −122, and ii) no C at position −144, and wherein the method further comprises genotyping said hepatitis C virus based on said 5' UTR genotype profile as Genotype I.

14. The method of claim 13, wherein said 5' UTR genotype profile further comprises: iii) no C at position −167.

15. The method of claim 1, wherein said 5' UTR genotype profile comprises: i) a T at position −122, and ii) a T at position −80, and wherein the method further comprises genotyping said hepatitis C virus based on said 5' UTR genotype profile as Genotype I.

16. The method of claim 15, wherein said 5' UTR genotype profile further comprises: iii) no C at position −167.

17. The method of claim 1, wherein said 5' UTR genotype profile comprises: i) a T at position −122, and ii) a C at position −72, and wherein the method further comprises genotyping said hepatitis C virus based on said 5' UTR genotype profile as Genotype I.

18. The method of claim 17, wherein said 5' UTR genotype profile further comprises: iii) no C at position −167.

19. The method of claim 1, wherein said 5' UTR genotype profile comprises: i) an A at position −132, and ii) a G at position −163, and wherein the method further comprises genotyping said hepatitis C virus based on said 5' UTR genotype profile as Genotype II.

20. The method of claim 1, wherein said 5' UTR genotype profile comprises: i) a T at position −245, and ii) a C at position −167, and wherein the method further comprises genotyping said hepatitis C virus based on said 5' UTR genotype profile as Genotype IV.

21. The method of claim 1, wherein said 5' UTR genotype profile comprises: i) a T at position −245, and ii) an A at position −118, and wherein the method further comprises genotyping said hepatitis C virus based on said 5' UTR genotype profile as Genotype IV.

22. The method of claim 1, wherein said 5' UTR genotype profile comprises: i) a T at position −167, ii) a G at position −163, and iii) a C at position −155, and wherein the method further comprises genotyping said hepatitis C virus based on said 5' UTR genotype profile as Genotype V.

23. The method of claim 1, wherein said 5' UTR genotype profile comprises: i) a C at position −122, and ii) a G at position −117, and wherein the method further comprises genotyping said hepatitis C virus based on said 5' UTR genotype profile as Genotype V.

24. The method of claim 1, wherein said 5' UTR genotype profile comprises: i) a G at position −117, and ii) a C at position −80, and wherein the method further comprises genotyping said hepatitis C virus based on said 5' UTR genotype profile as Genotype VI.

25. The method of claim 1, wherein said 5' UTR genotype profile comprises: i) an A at position −118, and ii) a C at position −80, and wherein the method further comprises genotyping said hepatitis C virus based on said 5' UTR genotype profile as Genotype VI.

26. The method of claim 1, wherein said 5' UTR genotype profile comprises: i) a T at position −122, and ii) a C at position −80, and wherein the method further comprises genotyping said hepatitis C virus based on said 5' UTR genotype profile as Genotype VI.

27. The method of claim 1, wherein said 5' UTR genotype profile comprises: i) a T at position −122, and ii) a T at position −72, and wherein the method further comprises genotyping said hepatitis C virus based on said 5' UTR genotype profile as Genotype VI.

* * * * *